US008828407B2

(12) United States Patent
Britton et al.

(10) Patent No.: US 8,828,407 B2
(45) Date of Patent: Sep. 9, 2014

(54) CHIMAERIC PROTEIN

(75) Inventors: Paul Britton, Hungerford (GB); Erica Bickerton, Oxford (GB); Maria Armesto, San Sebastian (ES)

(73) Assignee: The Pirbright Institute, Pirbright (GB)

( * ) Notice: Subject to any disclaimer, the term of this patent is extended or adjusted under 35 U.S.C. 154(b) by 198 days.

(21) Appl. No.: 13/382,119

(22) PCT Filed: Jul. 5, 2010

(86) PCT No.: PCT/GB2010/001293
§ 371 (c)(1),
(2), (4) Date: Mar. 29, 2012

(87) PCT Pub. No.: WO2011/004146
PCT Pub. Date: Jan. 13, 2011

(65) Prior Publication Data
US 2012/0177675 A1    Jul. 12, 2012

(30) Foreign Application Priority Data

Jul. 7, 2009  (GB) .................................. 0911794.6

(51) Int. Cl.
| | | |
|---|---|---|
| A61K 39/215 | (2006.01) |
| C12N 7/01 | (2006.01) |
| C12N 7/02 | (2006.01) |
| C12N 5/10 | (2006.01) |
| C12N 15/50 | (2006.01) |
| C07K 19/00 | (2006.01) |
| C07K 14/165 | (2006.01) |

(52) U.S. Cl.
USPC ................. 424/222.1; 424/192.1; 435/235.1; 435/239; 435/325; 435/364; 435/320.1; 536/23.4; 536/23.72

(58) Field of Classification Search
None
See application file for complete search history.

(56) References Cited

U.S. PATENT DOCUMENTS 7,445,785 B2    11/2008  Cavanagh et al.

FOREIGN PATENT DOCUMENTS

WO    WO-2004/078203 A2    9/2004

OTHER PUBLICATIONS

Casais et al (Journal of Virology 77:9084-9089, 2004).*
Chen et al (Avian Pathology 36:269-274, 2007).*
Ferriera et al (Avian Pathology 32:413-417, 2003).*
Casais et al (Journal of Virology 77:9084-9089, 2003) (in IDS).*
Hodgson et al (Journal of Virology 78:13804-13811, 2004).*
Altschul et al., Basic local alignment search tool, J. Mol. Biol., 215:403-10 (1990).
Armesto et al., Transient dominant selection for the modification and generation of recombinant infectious bronchitis coronaviruses, Methods Mol. Biol., 454:255-73 (2008).
Babcock et al., Amino acids 270 to 510 of the severe acute respiratory syndrome coronavirus spike protein are required for interaction with receptor, J. Virol., 78(9):4552-60 (2004).
Bonavia et al., Identification of a receptor-binding domain of the spike glycoprotein of human coronavirus HCoV-229E, J. Virol., 77(4):2530-8 (2003).
Bosch et al., The coronavirus spike protein is a class I virus fusion protein: Structural and functional characterization of the fusion core complex, J. Virol., 77(16):8801-11 (2003).
Britton et al., Generation of a recombinant avian coronavirus infectious bronchitis virus using transient dominant selection, J. Virol. Methods, 123(2):203-11 (2005).
Casais et al., Recombinant avian infectious bronchitis virus expressing a heterologous spike gene demonstrates that the spike protein is a determinant of cell tropism, J. Virol., 77(16):9084-9 (2003).
Casais et al., Reverse genetics system for the avian coronavirus infectious bronchitis virus, J. Virol., 75(24):12359-69 (2001).
Cavanagh et al., Manipulation of the infectious bronchitis coronavirus genome for vaccine development and analysis of the accessory proteins, Vaccine, 25(30):5558-62 (2007).
Compton et al., Coronavirus species specificity: murine coronavirus binds to a mouse-specific epitope on its carcinoembryonic antigen-related receptor glycoprotein, J. Virol., 66(12):7420-8 (1992).
de Haan et al., Cleavage of group 1 coronavirus spike proteins: how furin cleavage is traded off against heparan sulfate binding upon cell culture adaptation, J. Virol., 82(12):6078-83 (2008).
de Haan et al., Cooperative involvement of the S1 and S2 subunits of the murine coronavirus spike protein in receptor binding and extended host range, J. Virol., 80(22):10909-18 (2006).
de Haan et al., Murine coronavirus with an extended host range uses heparan sulfate as an entry receptor, J. Virol., 79(22):14451-6 (2005).
Delmas et al., Aminopeptidase N is a major receptor for the enteropathogenic coronavirus TGEV, Nature, 357:417-20 (1992).
Devereux et al., A comprehensive set of sequence analysis programs for the VAX, Nucleic Acids Res., 12(1):387-95 (1984).
Gagneten et al., Interaction of mouse hepatitis virus (MHV) spike glycoprotein with receptor glycoprotein MHVR is required for infection with an MHV strain that expresses the hemagglutinin-esterase glycoprotein, J. Virol., 69(2):889-95 (1995).

(Continued)

*Primary Examiner* — Mary E Mosher
(74) *Attorney, Agent, or Firm* — Marshall, Gerstein & Borun LLP

(57) ABSTRACT

The present invention provides a chimaeric coronavirus S protein which is based on an S protein from a coronavirus strain with restricted tissue tropism, but which comprises at least part of the S2 subunit from a coronavirus strain with extended tissue tropism, such that a virus comprising the chimaeric S protein has extended tissue tropism. The present invention also provides a virus comprising such a chimaeric S protein.

21 Claims, 15 Drawing Sheets

(56) References Cited

OTHER PUBLICATIONS

Godet et al., Major receptor-binding and neutralization determinants are located within the same domain of the transmissible gastroenteritis virus (coronavirus) spike protein, J. Virol., 68(12):8008-16 (1994).

International Preliminary Report on Patentability for corresponding International application No. PCT/GB2010/001293, issuance date Jan. 10, 2012.

International Search Report and Written Opinion from corresponding International application No. PCT/GB2010/001293, mailing date Oct. 19, 2010.

Kistner et al., Development of a mammalian cell (vero) derived candidate influenza virus vaccine, Vaccine, 16(9/10):960-8 (1998).

Koch et al., Antigenic domains on the peplomer protein of avian infectious bronchitis virus: correlation with biological functions, J. Gen. Virol., 71:1929-35 (1990).

Kubo et al., Localization of neutralizing epitopes and the receptor-binding site within the amino-terminal 330 amino acids of the murine coronavirus spike protein, J. Virol., 68(9):5403-10 (1994).

Li et al., Sequence analysis of nephropathogenic infectious bronchitis virus strains of the Massachusetts genotype in Beijing, Avian Pathology, 30(5):535-41 (2001).

Li et al., Structure of SARS coronavirus spike receptor-binding domain complexed with receptor, Science, 309(5742):1864-8 (2005).

Madu et al., Heparan sulfate is a selective attachment factor for the avian coronavirus infectious bronchitis virus Beaudette, Avian Dis., 51(1):45-51 (2007).

Rottier et al., Acquisition of macrophage tropism during the pathogenesis of feline infectious peritonitis is determined by mutations in the feline coronavirus spike protein, J. Virol., 79(22):14122-30 (2005).

Tan et al., Crystal structure of murine sCEACAM1a[1,4]: a coronavirus receptor in the CEA family, The EMBO J., 21(9):2076-86 (2002).

Tatusova et al., BLAST 2 Sequences, a new tool for comparing protein and nucleotide sequences, FEMS Microbiol. Lett., 174(2):247-50 (1999).

Thackray et al., Amino acid substitutions and an insertion in the spike glycoprotein extend the host range of the murine coronavirus MHV-A59, Virology, 324(2):510-24 (2004).

Winter et al., Sialic acid is a receptor determinant for infection of cells by avian infectious bronchitis virus, J. Gen. Virol., 87:1209-16 (2006).

Wong et al., A 193-amino acid fragment of the SARS coronavirus S protein efficiently binds angiotensin-converting enzyme 2, J. Biol. Chem., 279(5):3197-201 (2004).

Yamada et al., Proteolytic activation of the spike protein at a novel RRRR/S motif is implicated in furin-dependent entry, syncytia formation and infectivity of coronavirus infectious bronchitis virus in cultured cells, J. Virol., 38 pages (Jun. 24, 2009).

Yeager et al., Human aminopeptidase N is a receptor for human coronavirus 229E, Nature, 357:420-2 (1992).

* cited by examiner

Beaudette S gene from pGPT-IBV-StuI-BamHI

Rep | S1 | S2 | Gene 3
→ PCR ←

M41 S gene from pGPT-M41S

Rep | S1 | S2 | Gene 3
→ PCR ←

↓

S1
||||
S2

→ Overlapping PCR ←

↓

NsiI ↑ | S1 | S2 | ↑ BspEI
Chimaeric S gene

Ligation ↓ gpt
S1 | S2

---

Beaudette S gene from pGPT-IBV-StuI-BamHI

Rep | S1 | S2 | Gene 3
→ PCR ←

M41 S gene from pGPT-M41S

Rep | S1 | S2 | Gene 3
→ PCR ←

↓

S1
||||
S2

→ Overlapping PCR ←

↓

NsiI ↑ | S1 | S2 | ↑ BspEI
Chimaeric S gene

Ligation ↓ gpt
S1 | S2

FIG. 3

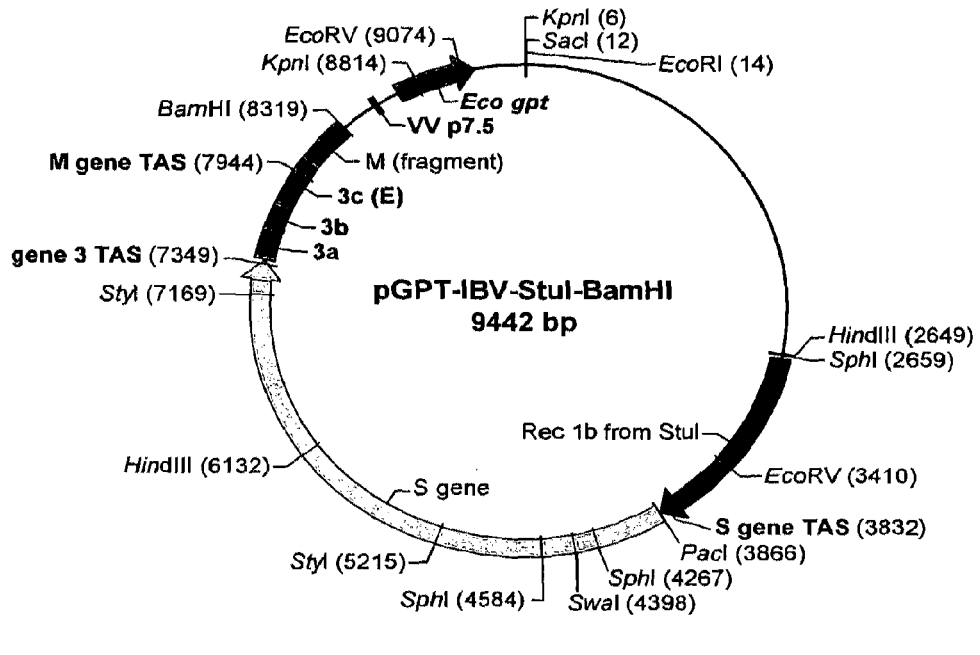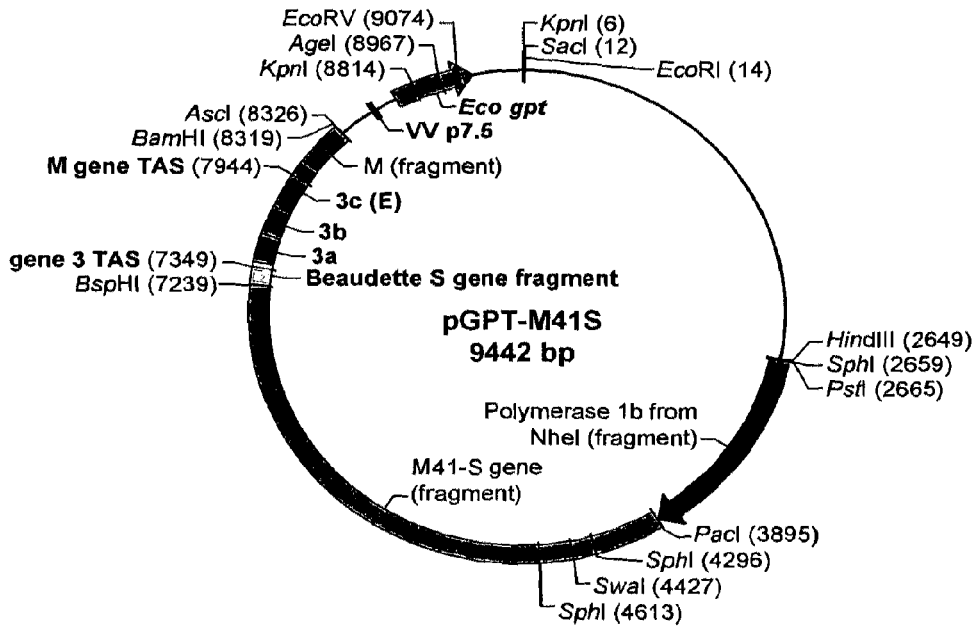
FIG. 4

Beau-R       : SEQ ID NO: 2
Beau-R-Hep-Mod: SEQ ID NO: 3
M41-Hep-Mod  : SEQ ID NO: 4
M41          : SEQ ID NO: 5

Please note:-

Beau-R corresponds to Beaudette that grows on Vero cells and has the potential heparan sulphate binding site
M41 does not grow on Vero cells and does not have the potential heparan sulphate binding site
Beau-R-Hep-Mod has the modified sequence that has potential heparan sulphate binding site modified to the corresponding M41 sequence.
M41-Hep-Mod has the modified sequence that has Beaudette potential heparan sulphate binding site introduced into the M41 sequence.

```
             *        20         *        40         *        60         *        80
Beau-CK : MLVTPLLLVTLLCALCSAVLYDSSSYVYYYQSAFRPPNGWHLQGGAYAVVNISSEFNNAGSSSGCTVGIIGGGRVVNASS
M41-CK  : MLVTPLLLVTLLCVLCSAALYDSSSYVYYYQSAFRPPNGWHLHCGAYAVVNISSESNNAGSSPGCIVGTIHGGRVVNASS

*       100         *       120         *       140         *       160
Beau-CK : IAMTAPSSGMAWSSSQFCTAHCNFSDTTVFVTHCYKHGGCPLTGMLQQHLIRVSAMKNGQLFYNITVSVAKYPTFRSPQC
M41-CK  : IAMTAPSSGMAWSSSQFCTAHCNFSDTTVFVTHCYKYDGCPITGMLQKNFLRVSAMKNGQLFYNLTVSVAKYPTFKSPQC

*       180         *       200         *       220         *       240
Beau-CK : VNNLTSVYLNGDLVYTSNETIDVTSAGVYFKAGGPITYKVNREVKALAYFVNGTAQDVILCDGSPRGLLACQYNTGNFSD
M41-CK  : VNNLTSVYLNGDLVYTSNETTDVTSAGVYFKAGGPITYKVNREVKALAYFVNGTAQDVILCDGSPRGLLACQYNTGNFSD

*       260         *       280         *       300         *       320
Beau-CK : GFYPFTNSSLVKQKFIVYRENSVNTTCTLHNFTFHNETGANPNFSGVQNIQTYQTKTAQSGYYNFNFSFLSSFVYKESNF
M41-CK  : GFYPFINSSLVKQKFIVYRENSVNTTFTLHNFETFHNETGANPNFSGVQNIQTYQTQTACSGYYNFNFSFLSSFVYKESNF

*       340         *       360         *       380         *       400
Beau-CK : MYGSYHPSCKFRLETINNGLWFNSLSVSIAYGPLQGGCKQSVFKGRATCCYAYSYGGPSLCKGVYSGELDHNFECGLLVY
M41-CK  : MYGSYHPSCNFRLETINNGLWFNSLSVSIAYGPLQGGCKQSVFSGRATCCYAYSYGGPSLCKGVYSGELDLNFECGLLVY

*       420         *       440         *       460         *       480
Beau-CK : VTKSGGSRIQTATEPPVITQNNNGNNITLNTCVDYNIYGRTGQGFITNVTDSAVSYNYLADAGLAILDTSGSIDIFVVQGE
M41-CK  : VTKSGGSRIQTATEPPVITRHNYNNITLNTCVDYNIYGRTGQGFITNVTDSAVSYNYLADAGLAILDTSGSIDIFVVQGE

*       500         *       520         *       540         *       560
Beau-CK : YGLNYYKVNPCEDVNQQFVVSGGKLVGILTSRNETGSQLLENQFYIKITNGTRRFRRSITENVANCPYVSYGKFCIKPDG
M41-CK  : YGLTYYKVYPCEDVNQQFVVSGGKLVGILTSRNETGSQLLENQFYIKITNGTRRERRSITENVANCPYVSYGKFCIKPDG

*       580         *       600         *       620         *       640
Beau-CK : SIATIVPKQLEQFVAPLFNVTENVLIPNSFNLTVTDEYIQTRMDKVQINCLQYVCGSSLDCRKLFQQYGPVCDNILSVVN
M41-CK  : SIATIVPKQLEQFVAPLLVTENVLIPNSFNLEVIDEYIQTRMDKVQINCMQYVCGNSLDCRDLFQQYGPVCDNILSVVN

*       660         *       680         *       700         *       720
Beau-CK : SVGQKEDMELLNFYSSTKPAGFNTPVLSNVSTGEFNISLLLTNPSSRRKRSLIEDLLFTSVESVGLPTNDAYKNCTAGPL
M41-CK  : SIGQKEDMELLNFYSSTKPAGFNTPFLSNVSTGEFNISLLLTTPSSPRRESFIEDLLFTSVESVGLPTDDAYKNCTAGPL

*       740         *       760         *       780         *       800
Beau-CK : GFFKDLACAREYNGLLVLPPIITAEMQALYTSSLVASMAFGGITAAGAIPFATQLQARINHLGITQSLLLKNQEKIAASF
M41-CK  : GFLKDLACAREYNGLLVLPPIITAEMQTLYTSSLVASMAFGGITAAGAIPFATQLQARINHLGITQSLLLKNQEKIAASF

*       820         *       840         *       860         *       880
Beau-CK : NKAIGHMQEGFRSTSLALQQIQDVVNKQSAILTETMASLNKNFGAISSVIQEIYQQFDATQANACVDRLITGRLSSLSVL
M41-CK  : NKAIGRMQEGFRSTSLALQQIQDVVNKQSAILTETMASLNKNFGAISSMIQEIYQQLDATQANACVDRLITGRLSSLSVL

*       900         *       920         *       940         *       960
Beau-CK : ASAKQAEYIRVSQQRELATQKINECVKSQSIRYSFCGNGRHVLSIPQNAPNGIVFIHFSYTPDSFVNVTAIVGFCVKPAN
M41-CK  : ASAKQAEHIRVSQQRELATQKINECVKSQSIRYSFCGNGRHVLTIPQNAPNGIVFIHFSYTPDSFVNVTAIVGFCVKPAN

*       980         *      1000         *      1020        1030        1040
Beau-CK : ASQYAIVPANGRGIFIQVNGSYYITARDMYMPRAITAGDIVTLTSCQANYVNVNKTVITTFVDNDDFDFDDELSKWWNDT
M41-CK  : ASQYAIVPANGRGIFIQVNGSYYITARDMYMPRAITAGDIVTLTSCQANYVSVNKTVITTFVDNDDFDFDDELSKWWNDT

*      1060         *      1080         *      1100         *      1120
Beau-CK : KHELPDFDKFNYTVPILDIDSEIDRIQGVIQGLNDSLIDLEKLSIIKTYIKWPWYVWLAIAFATIIFILILGWVFFMTGC
M41-CK  : KHELPDFDKFNYTVPILDIDSEIDRIQGVIQGLNDSLIDLEKLSIIKTYIKWPWYVWLAIAFATIIFILILGWVFFMTGC

*      1140         *      1160
Beau-CK : CGCCCCFGIMPLMSKCGKKSSYYTTFDNDVVTEQYRPKKSV
M41-CK  : CGCCCCFGIMPLMSKCGKKSSYYTTFDNDVVT---------

Beau-CK :SEQ ID NO: 1
M41-CK  :SEQ ID NO: 6
```

FIG. 12a

```
                   *        20         *        40         *        60         *        80
Beau-CK    FRRSITENVANCPYVSYGKFCIKPDGSIATIVPKQLEQFVAPLFNVTENVLIPNSFNLTVTDEYIQTRMDKVQINCLQYV
M41-CK     FRRSITENVANCPYVSYGKFCIKPDGSIATIVPKQLEQFVAPLLNVTENVLIPNSFNLTVTDEYIQTRMDKVQINCMQYV

*        100        *        120        *        140        *        160
Beau-CK    CGSSIDCRKLFQQYGPVCDNILSVVNSVGQKEDMELLNFYSSTKPAGFNTPVLSNVSTGEFNISLLLTNPSSRRKRSLIE
M41-CK     CGNSLDCRDLFQQYGPVCDNILSVVNSIGQKEDMELLFYSSTKPAGFNIPFLSNVSTGEFNISLLLTTESSPRRRSFIE

*        180        *        200        *        220        *        240
Beau-CK    DLLFTSVESVGLPTNDAYKNCTAGPLGFFKDLACAREYNGLLVLPPIITAEMQALYTSSLVASMAFGGITAAGAIPFATQ
M41-CK     DLLFTSVECVGLPTDDAYKNCTAGPLGFLKDLACAREYNGLLVLPPIITAEMQTLYTSSLVASMAFGGITAAGAIPFATQ

*        260        *        280        *        300        *        320
Beau-CK    LQARINHLGITQSLLLKNQEKIAASFNKAIGHMQEGFRSTSLALQQIQDVVSKQSAILTETMASLNKNFGAISSVIQEIY
M41-CK     LQARINHLGITQQLLLKNQEKIAASINKAIGRMQEGFRSTSLALQQIQDVVNKQSAILTETMASLNKNFGAISSMIQEIY

*        340        *        360        *        380        *        400
Beau-CK    QQFDAIQANAQVDRLITGRLSSLSVLASAKQAEYIRVSQQRELATQKINECVKSQSIRYSFCGNGRHVLTIPQNAPNGIV
M41-CK     QQLDAIQANAQVDRLITGRLSSLSVLASAKQAEHIRVSQQRELATQKINECVKSQSIRYSFCGNGRHVLTIPQNAPNGIV

*        420        *        440        *        460        *        480
Beau-CK    FIHFSYTPDSFVNVTAIVGFCVKPANASQYAIVPANGRGIFIQVNGSYYITARDMYMPRAITAGDVVTLTSCQANYVSVN
M41-CK     FIHFSYTPDSFVNVTAIVGFCVKPANASQYAIVPANGRGIFIQVNGSYYITARDMYMPRAITAGDIVTLTSCQANYVSVN

*        500        *        520        *        540        *        560
Beau-CK    KTVITTFVDNDDFDFNDELSKWWNDTKHELPDFDKFNYTVPILDIDSEIDRIQGVIQGLNDSLIDLEKLSILKTYIKWPW
M41-CK     KTVITTFVDNDDFDFNDELSKWWNDTKHELPDFDKFNYTVPILDIDSEIDRIQGVIQGLNDSLIDLEKLSILKTYIKWPW

*        580        *        600        *        620
Beau-CK    YVWLAIAFATIIFILILGWVFFMTGCCGCCCGCFGIMPLMSKCGKKSSYYTTFDNDVVTEQYRPKKSV
M41-CK     YVWLAIAFATIIFILILGWVFFMTGCCGCCCGCFGIMPLMSKCGKKSSYYTTFDNDVVT---------

Beau-CK    :SEQ ID NO: 7
M41-CK     :SEQ ID NO: 8
```

Numbers refer to the position of the amino acid differences they have devised a chimaeric S protein which, when used to produce a virus, causes the virus to have extended tissue tropism.

CHIMAERIC PROTEIN

CROSS-REFERENCE TO RELATED APPLICATIONS

This application is a 35 U.S.C. §371 National filing of International Application No. PCT/GB2010/001293, filed Jul. 5, 2010, incorporated herein by reference, which claims priority benefit of Great Britain patent application No. 0911794.6, filed Jul. 7, 2009.

FIELD OF THE INVENTION

The present invention relates to a chimaeric coronavirus S protein. In particular a chimaeric coronavirus S protein which, when used to produce a virus, causes the virus to have extended tissue tropism. The present invention also relates to nucleotide sequences encoding such a chimaeric protein; viral particles comprising such a chimaeric protein and their use in a vaccine to prevent and/or treat a disease.

BACKGROUND TO THE INVENTION

Infectious Bronchitis Virus (IBV)

Avian infectious bronchitis virus (IBV) is a highly infectious and contagious pathogen of domestic fowl that replicates primarily in the respiratory tract but also in epithelial cells of the gut, kidney and oviduct. IBV is a member of the Coronaviridae and genetically very similar coronaviruses cause disease in turkeys and pheasants.

Clinical signs of IB include sneezing, tracheal rales, nasal discharge and wheezing. Meat-type birds have reduced weight gain, whilst egg-laying birds lay fewer eggs. The respiratory infection predisposes chickens to secondary bacterial infections which can be fatal in chicks. The virus can also cause permanent damage to the oviduct, especially in chicks, leading to reduced egg production and quality; and kidney, sometimes leading to kidney disease which can be fatal.

Both live and attenuated vaccines are currently used in IB vaccination. To date, the most efficacious vaccines are live attenuated viruses empirically produced following blind repeated passages through embryonated eggs.

A problem with this approach is that, upon serial passaging, the immunogenicity of the virus decreases. It is necessary to achieve a balance between an acceptable degree of attenuation to make the virus safe, and an acceptable loss of immunogenicity such that the virus vaccine is still efficacious. This "balancing" of attenuation is a trial and error approach, rendering the outcome of the attenuation process uncertain.

Since attenuation by serial passage is effectively a random event, the resultant vaccine is ill-defined genetically as the molecular basis of the attenuation is unknown. Each batch of attenuated virus will be different, making it difficult to achieve consistency of the resulting vaccine and reproducibility of the protective/therapeutic effect in vivo.

A further disadvantage is that embryonated eggs are expensive and cannot be used as a prolonged source of virus.

Growth of virus on embryonated eggs is a cumbersome process as each egg must be sterilized, candled, inoculated with virus and incubated before harvesting small volumes of allantoic fluid from each egg and pooling before purification. The lack of reliable supplies of high quality eggs results in limitations in the amount of vaccine which may be produced, particularly in an emergency situation.

In addition to these logistic and supply problems, embryonated eggs have other limitations as a host system for vaccine production. For example, there are increasing concerns about the presence of adventitious viruses, particularly retroviruses in eggs, which would compromise the production of live, attenuated viral vaccines.

There is therefore a need for alternative IBV vaccines and methods for their production which do not suffer from the above mentioned drawbacks.

Coronaviruses

Coronaviruses are enveloped viruses that replicate in the cell cytoplasm and contain an unsegmented, single-stranded, positive sense RNA genome of 27 to 32 kb.

All coronavirus lipid envelopes contain at least three membrane proteins: the spike glycoprotein (S), integral membrane protein (M), and small membrane protein (E). The coronavirus S protein is a type I glycoprotein which oligomerizes in the endoplasmic reticulum and is assembled into virion membranes through non-covalent interactions with the membrane protein. Following incorporation into coronavirus particles, the S protein is responsible for binding to the target cell receptor and fusion of the viral and cellular membranes. The S glycoprotein consists of four domains: a signal sequence that is cleaved during synthesis; the ectodomain, which is present on the outside of the virion particle; the transmembrane region responsible for anchoring the S protein into the lipid bilayer of the virion particle; and the cytoplasmic tail.

The IBV S protein (1,162 amino acids) is cleaved into two subunits, S1 (535 amino acids; 90 kDa) comprising the N-terminal half of the S-protein, and S2 (627 amino acids; 84 kDa) comprising the C-terminal half of the S protein.

The S2 protein subunit associates non-covalently with the S1 subunit and contains the transmembrane and C-terminal cytoplasmic tail domains.

The S1 subunit has been widely reported to comprise the receptor-binding activity of the S protein.

For example, it has been shown for the serogroup I coronavirus, human coronavirus HCoV-229E, that of three variants having truncation in the N-terminal domain of S1, two were unable to bind the receptor, implicating the region between amino acids 417 and 547 as important for receptor binding (Bonavia et al (2003) J. Virol 77. 2530-2538).

The first 330 amino acids of the 769-residue S1 subunit of the mouse hepatitis virus (MHV) S protein are sufficient to bind the MHV receptor (Kubo et al (1994) J. Virol. 68:5403-5410). Similarly an 193-amino acid fragment of the SARS S protein (residues 318-510) binds to the receptor and blocks S-protein mediated infection (Wong et al (2004) J. Biol. Chem. 279:3197-3201).

It is also reported that amino acids 1-510 of the SARS-CoV S glycoprotein represent a domain containing the receptor binding site (amino acids 270-510) analogous to the S1 subunit of other coronavirus S glycoproteins (Babcock et al (2004) J. Virol. 4552-4560).

The S protein is a determinant of the cell tropism of the virus (Casias et al (2003) J. Virol. 77:9084-9089). It has been shown that amino acid substitutions in the N-terminal region of the S1 protein are associated with the extended host range of a virus variant of murine hepatitis virus (MHV) (Thackray and Holmes (2004) Virology 324:510-524). Moreover, it is generally thought that species specificity of infection is due to the specificity of the virus-receptor interaction (Compton et al (1992) J. Virol. 7420-7428; Gagneten et al (1995) J. Virol. 69:889-895).

It has, to date, thus been widely assumed that cell tropism is a property of the S1 domain of the S protein of coronaviruses.

SUMMARY OF ASPECTS OF THE INVENTION

The present inventors have surprisingly shown that cell tropism of coronaviruses is determined by the S2 protein, and that substitution of the S2 protein with all or part of another coronavirus can alter (extend or reduce) the cell tropism of the virus, depending on the cell tropism of the virus from which the S2 protein was derived.

This means that immunogenic virus vaccines which are unable to grow on cell lines can be induced to do so by substitution of all or part of their S2 proteins.

Thus, in a first aspect, the present invention provides a chimaeric coronavirus S protein which is based on an S protein from a coronavirus strain with restricted tissue tropism, but which comprises at least part of the S2 subunit from a coronavirus strain with extended tissue tropism, such that a virus comprising the chimaeric S protein has extended tissue tropism.

The chimaeric S protein may comprise all or part of the S2 subunit from the coronavirus strain with extended tissue tropism.

For example, a chimaeric infectious bronchitis virus (IBV) S protein may comprise a portion of the S2 sequence which comprises the sequence XBBXBX (SEQ ID NO: 9) in the part of the S2 protein corresponding to between residues 686 and 691 of the sequence given as SEQ ID No. 1, where B is a basic residue and X is any amino acid.

The sequence XBBXBX (SEQ ID NO: 9) may, for example, be the sequence SRRKRS (SEQ ID NO: 10) or SRRRRS (SEQ ID NO: 11). The chimaeric S protein may comprise the sequence SRRKRSLIE (SEQ ID NO: 12) or SRRRRSVIE (SEQ ID NO: 13) in the part of the S2 protein corresponding to between residues 686 and 694 of the sequence given as SEQ ID No. 1.

The coronavirus may, for example be: Infectious bronchitis virus (IBV); Canine coronavirus (CCoV); Feline coronavirus (FeCoV); Human coronavirus 229E (HCoV-229E); Porcine epidemic diarrhoea virus (PEDV); Transmissible gastroenteritis virus (TGEV); Human Coronavirus NL63 (NL or New Haven); Bovine coronavirus (BCoV); Canine respiratory coronavirus (CRCoV); Human coronavirus OC43 (HCoV-OC43); Mouse hepatitis virus (MHV); Porcine haemagglutinating encephalomyelitis virus (HEV); Rat coronavirus (RCV); Turkey coronavirus (TCoV); HCoV-HKU1; Severe acute respiratory syndrome coronavirus (SARS-CoV); or Turkey coronavirus (Bluecomb disease virus).

Where the coronavirus is IBV, the IBV strain with extended tissue tropism may be IBV Beaudette.

In a second aspect, the present invention provides a nucleotide sequence capable of encoding a chimaeric S protein according to the first aspect of the invention.

The invention also provides plasmid comprising a nucleotide sequence according to the second aspect of the invention.

In a third aspect, the present invention provides a viral particle comprising a chimaeric S protein according to the first aspect of the invention, and/or a nucleotide sequence according to the second aspect of the invention.

The viral particle may be a recombinant vaccinia virus (rVV) or a coronavirus.

The viral particle may be capable of growing on a cell line such as Vero cells.

The infection of Vero cells by a viral particle according to the third aspect of the invention may be blocked by soluble heparin.

In a fourth aspect, the present invention provides a method for making a viral particle according to the third aspect of the invention a method for making a viral particle by:

(i) transfecting a plasmid as described in the previous section into a host cell;
(ii) infecting the host cell with a recombining virus comprising the genome of the coronavirus strain with restricted tissue tropism, minus at least part of the S2 subunit;
(iii) allowing homologous recombination to occur between the S gene sequences in the plasmid and the corresponding sequences in the recombining virus genome to produce a chimaeric S gene; and
(iv) selecting for recombining virus comprising the chimaeric S gene.

The recombining virus may be vaccinia virus.

In order to generate a recombinant coronavirus particle, the virus DNA from step (iv) may be used to generate coronavirus RNA in situ using a reverse genetics system.

The above method therefore optionally includes the step:

(v) recovering recombinant coronavirus comprising the chimaeric S gene from the DNA from the recombining virus from step (iv).

In a fifth aspect, the present invention provides a cell capable of producing a viral particle according to the fourth aspect of the invention. The cell may, for example, be a cell, such as a primary chick kidney cell, capable of producing recombinant virus using a reverse genetics system, or a cell infected with a viral particle according to the fourth aspect of the invention.

The cell infected with a viral particle according to the fourth aspect of the invention may be derivable from a cell line, such as a Vero cell.

In a sixth aspect, the present invention provides a vaccine comprising a viral particle of the fourth aspect of the invention.

Further aspects of the invention provide:

(i) a method for treating and/or preventing a disease in a subject which comprises the step of administering a vaccine according to the sixth aspect of the invention to the subject;
(ii) a vaccine according to the sixth aspect of the invention for treating and/or preventing a disease in a subject;
(iii) the use of a viral particle according to the fourth aspect of the invention in the manufacture of a vaccine for treating and/or preventing a disease in a subject.
(iv) a method for producing a vaccine according to the sixth aspect of the invention, which comprises the step of infecting Vero cells with a viral particle according to the fourth aspect of the invention;
(v) a method for altering the cell tropism of a coronavirus which comprises the step of substitution of at least a part of the S2 protein with the S2 protein, or corresponding part thereof, from a different strain; and
(vi) a cell culture comprising a cell or a population of cells according to the fifth aspect of the invention.

The extended cell tropism conferred on the virus by the presence of the chimaeric gene means that virus stock for vaccine production can be produced by growing on cell lines, rather than embryonated eggs or primary cells.

The use of cell lines such as Vero cell has many advantages:

(i) it has been previously validated for growth of viruses and diagnostic purposes;
(ii) the cells (and therefore virus) can be grown in suspension, rather than flat beds; and
(iii) it is possible to achieve consistent yields.

DESCRIPTION OF THE FIGURES

FIG. 3—Generation of plasmids containing chimaeric S glycoprotein genes. The S1 and S2 subunits of Beau-R and M41 were amplified from two plasmids, pGPT-M41S and pGPT-IBV-StuI-BamHI, by PCR using primers located in the replicase gene, across the S1/S2 junction and gene 3. Overlapping PCR was used to combine the subunits, forming the chimaeric S genes, which were then cut with NsiI (restriction site located in the replicase gene) and BspEI (restriction site located in gene 3). The receiver plasmid, pGPT-IBV-StuI-BamHI, was also cut with NsiI and BspEI and the Beaudette S gene was removed by gel extraction. The chimaeric S genes were ligated into the remaining pGPT-IBV-StuI-BamHI backbone containing the *E. coli* guanine xanthine phosphoribosyltransferase (gpt) gene.

FIG. 4—Diagrams of pGPT-IBV-StuI-BamHI and pGPT-M41S.

The plasmids pGPT-IBV-StuI-BamHI and pGPT-M41S were used to amplify the Beau-R and M41 S1 and S2 subunits by PCR. The replicase gene and gene 3 surrounding the S genes are derived from Beaudette. The C-terminus of the M41 S gene in pGPT-M41 S has been exchanged for the Beau-R S gene C-terminus because this is the area that interacts with the M protein. The C-terminal ends of the M41 and Beau-R S proteins are very different to each other so to enable interaction of the chimaeric S protein with the other structural proteins from Beau-R, it was decided to keep the Beau-R S gene C-terminus. The Beau-R S gene was removed from pGPT-IBV-StuI-BamHI and the chimaeric S genes inserted in its place to create the plasmids pGPT-S1$_{M41}$S2$_{Beau}$ and pGPT-S1$_{Beau}$S2$_{M41}$.

Figure 5:
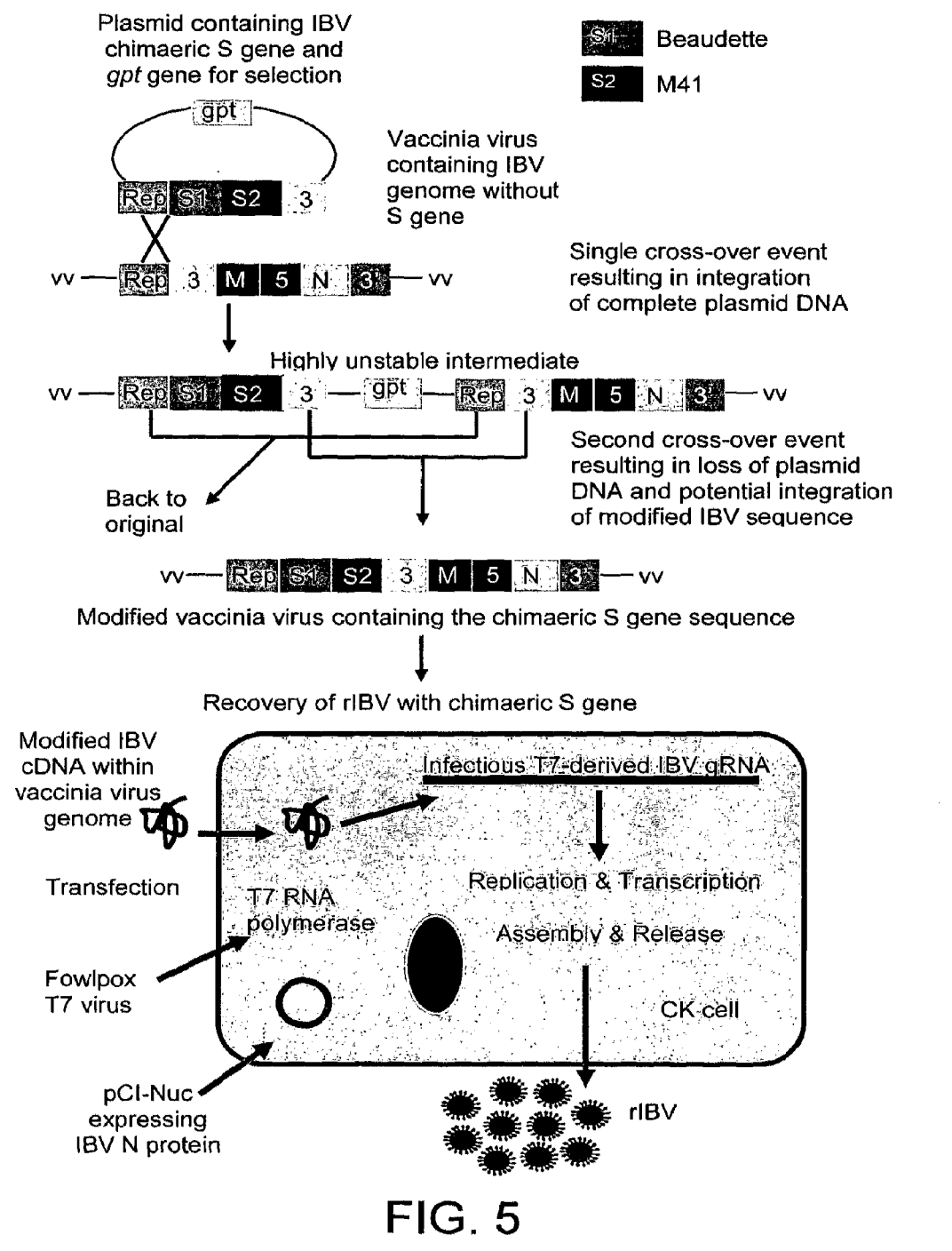

FIG. 5—The IBV reverse genetics system.

A plasmid vector containing gpt is constructed from the chimaeric S gene and parts of the neighbouring genes in the IBV genome. The plasmid is transfected into Vero cells infected with rVV containing the IBV genome minus the S gene. Three rounds of plaque purification in the presence of gpt selection components and three rounds in absence are carried out to select for rVV containing the chimaeric S gene. Large virus stocks are prepared in BHK-21 cells from which virus is purified and DNA extracted. Recombinant IBV cDNA within the VV genome and a plasmid expressing the IBV N protein are transfected into CK cells infected with rFPV-T7. The supernatant is filtered and used for passage on CK cells and rIBV with the chimaeric S gene is recovered.

Figure 6:
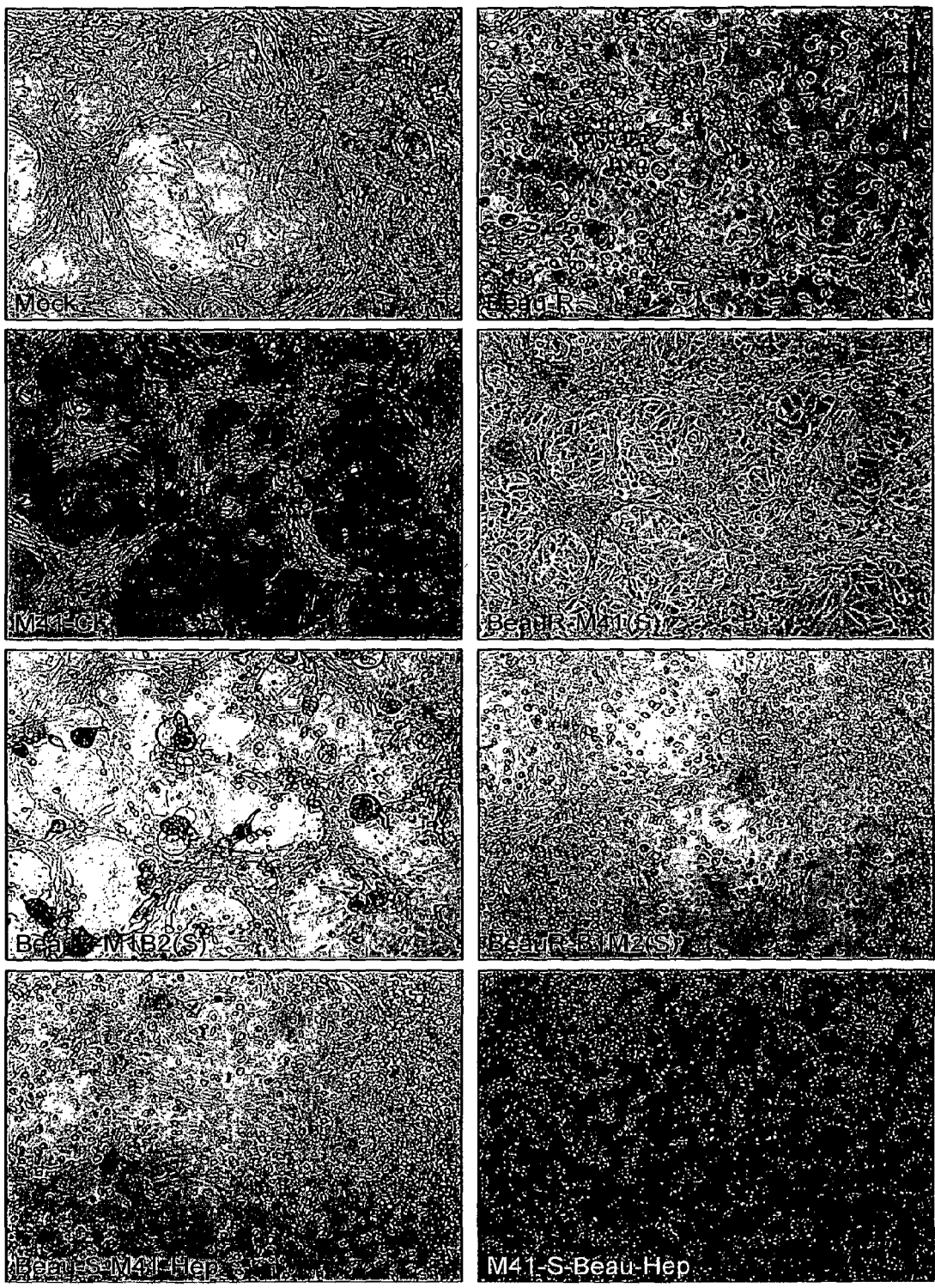

FIG. 6—Infected Vero cells 48 hours post-infection with various IBVs.

Figure 7:
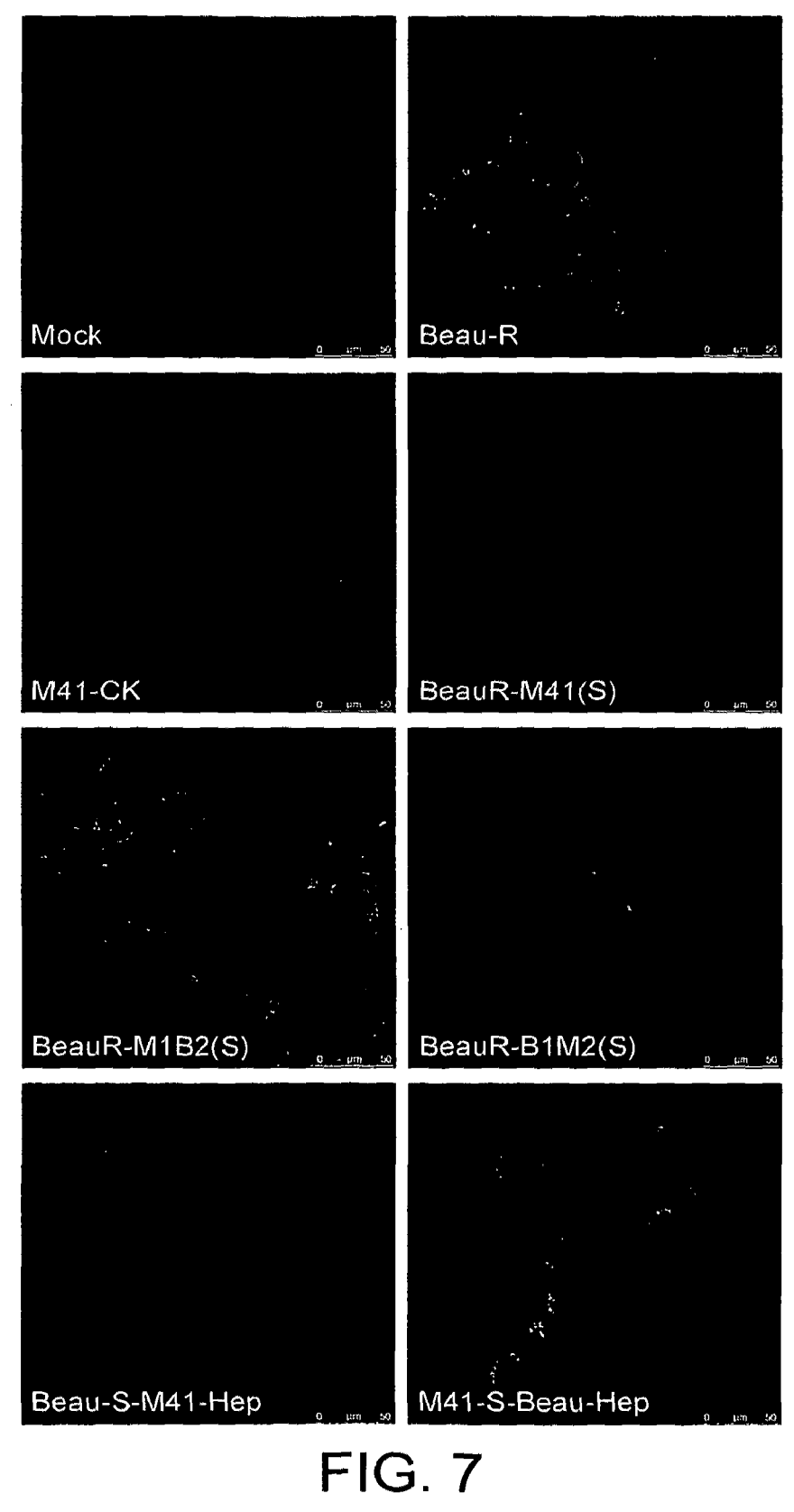

FIG. 7—Confocal microscopy of rIBV growth on Vero cells. Vero cells were infected with rIBVs and were fixed 24 hours post-infection and immunolabelled with mouse anti-dsRNA, secondary antibody AlexaFluor 488 goat anti-mouse (green, Invitrogen) to detect IBV infected cells. Nuclei of all the cells were labelled with DAPI (blue).

Figure 8:
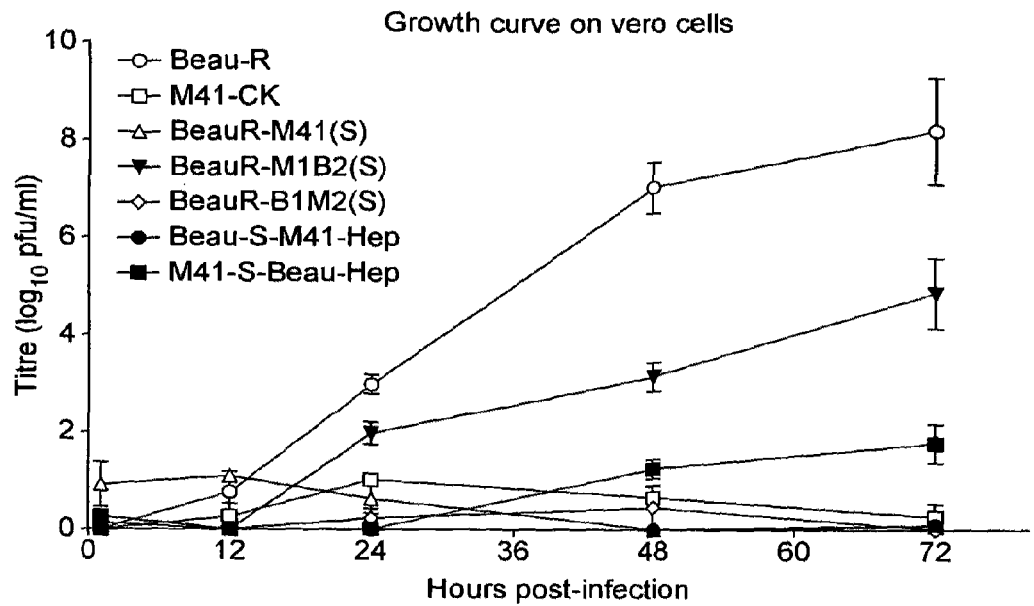

FIG. 8—Growth kinetics of rIBVs on Vero cells. Vero cells were infected with Beau-R, M41-CK, BeauR-M41(S), BeauR-M1B2(S), BeauR-B1M2(S), Beau-S-M41-Hep and M41-S-Beau-Hep at a multiplicity of infection of 0.1. Supernatant was harvested at 1, 12, 24, 48 and 72 hours post-infection and titrated on CK cells. Three replicates were performed and the averages taken. Error bars indicate standard error of the mean.

Figure 9:
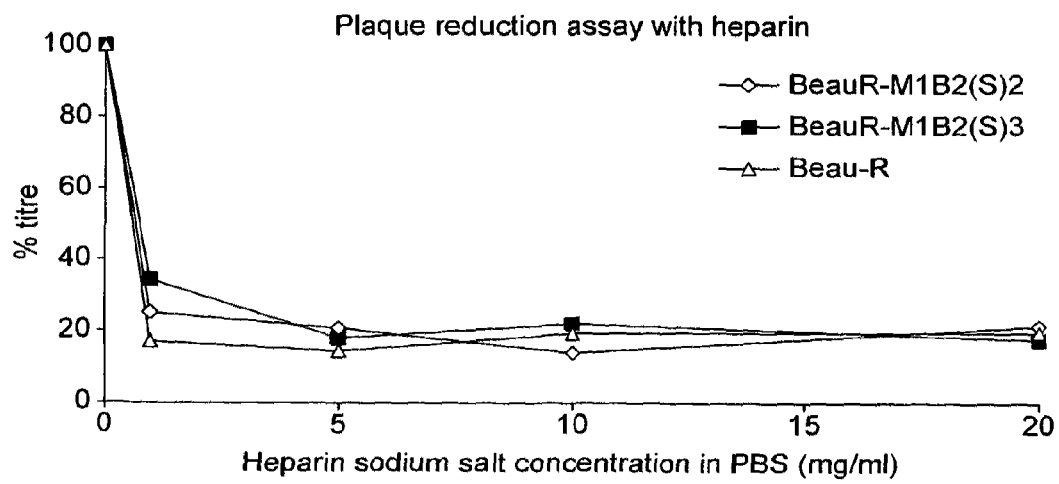

FIG. 9—Plaque reduction assay on Vero cells of IBV pretreated with increasing amounts of soluble heparin.

Figure 10:
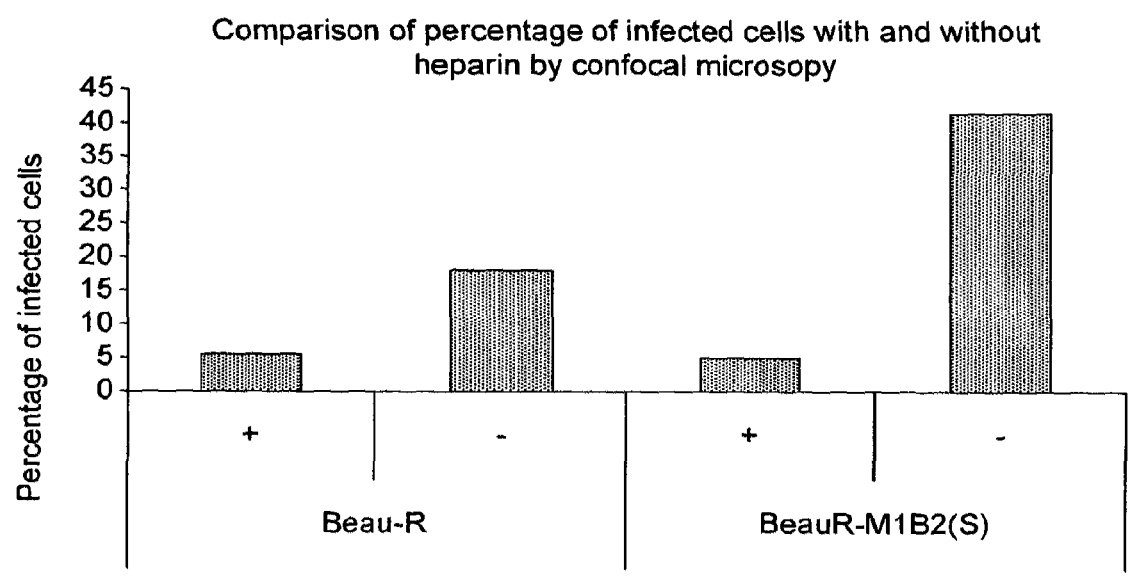

FIG. 10—Bar chart comparing the effect of soluble heparin on the percentage of IBV-infected Vero cells. IBV strains Beau-R and BeauR-M1B2(S) were incubated with either PBS (−) or soluble heparin, 15 mg/ml (+) for 30 minutes at room temperature prior to infecting Vero cells. Cells were fixed 24 hours post-infection then immunolabelled with mouse α-dsRNA, secondary antibody goat α-mouse IgG (green, Invitrogen) and nuclei were stained blue with DAPI. Ten fields of vision per sample were analysed by confocal microscopy at ×40 magnification and the percentage of infected cells was calculated.

Figure 11:
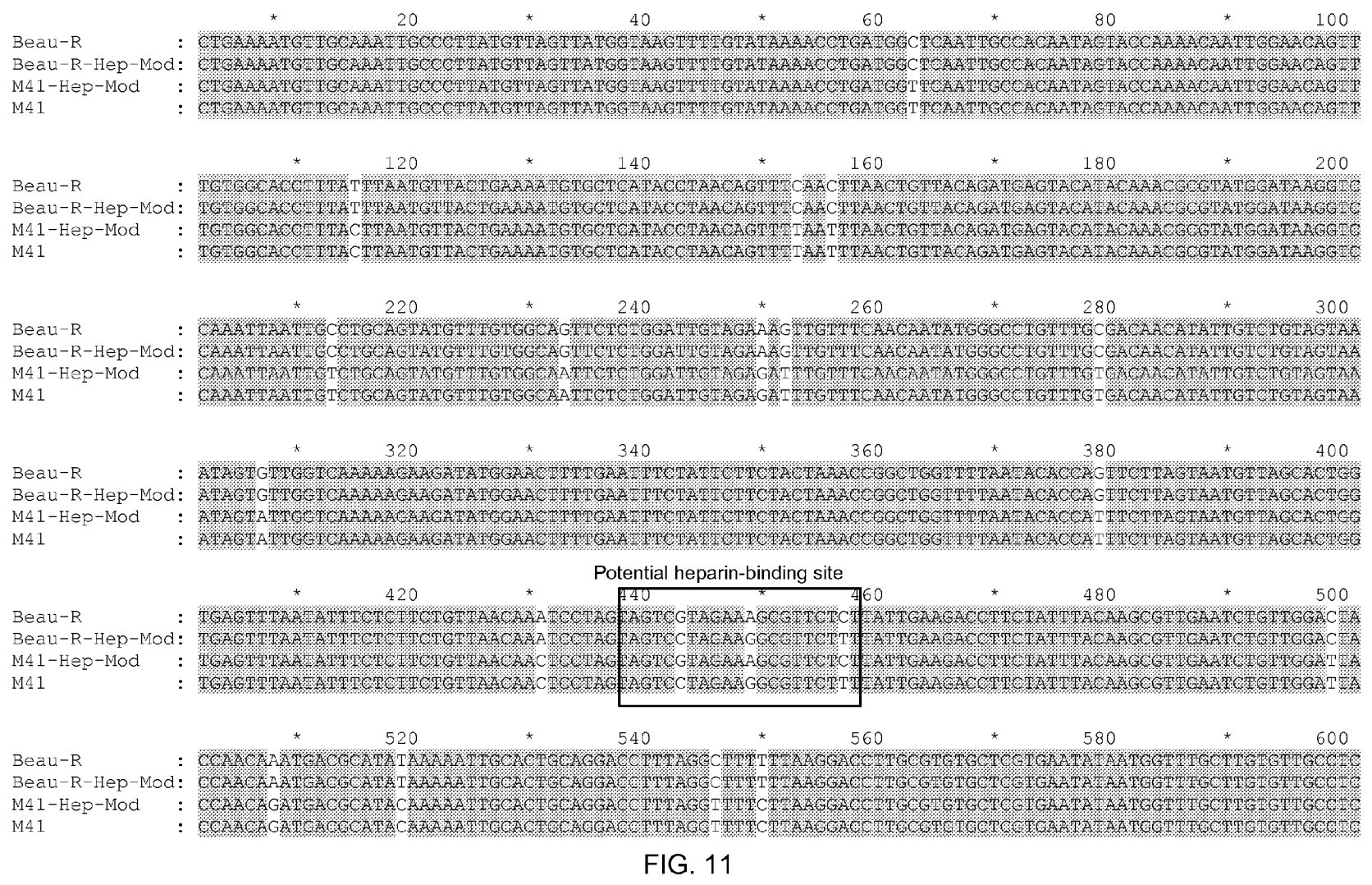

FIG. 11—Alignment between Beaudette (Beau-R), M41, Beaudette having the heparan-sulphate-binding site modified to the corresponding M41 sequence (Beau-S-M41-Hep) and M41 having the Beaudette heparan-sulphate-binding site (M41-S-Beau-Hep)

FIG. 12—Comparison of Beaudette and M 41 a) S protein sequences, and b) S2 region.

FIG. 13—Amino acid differences between M41 and Beaudette S proteins.

Figure 14:
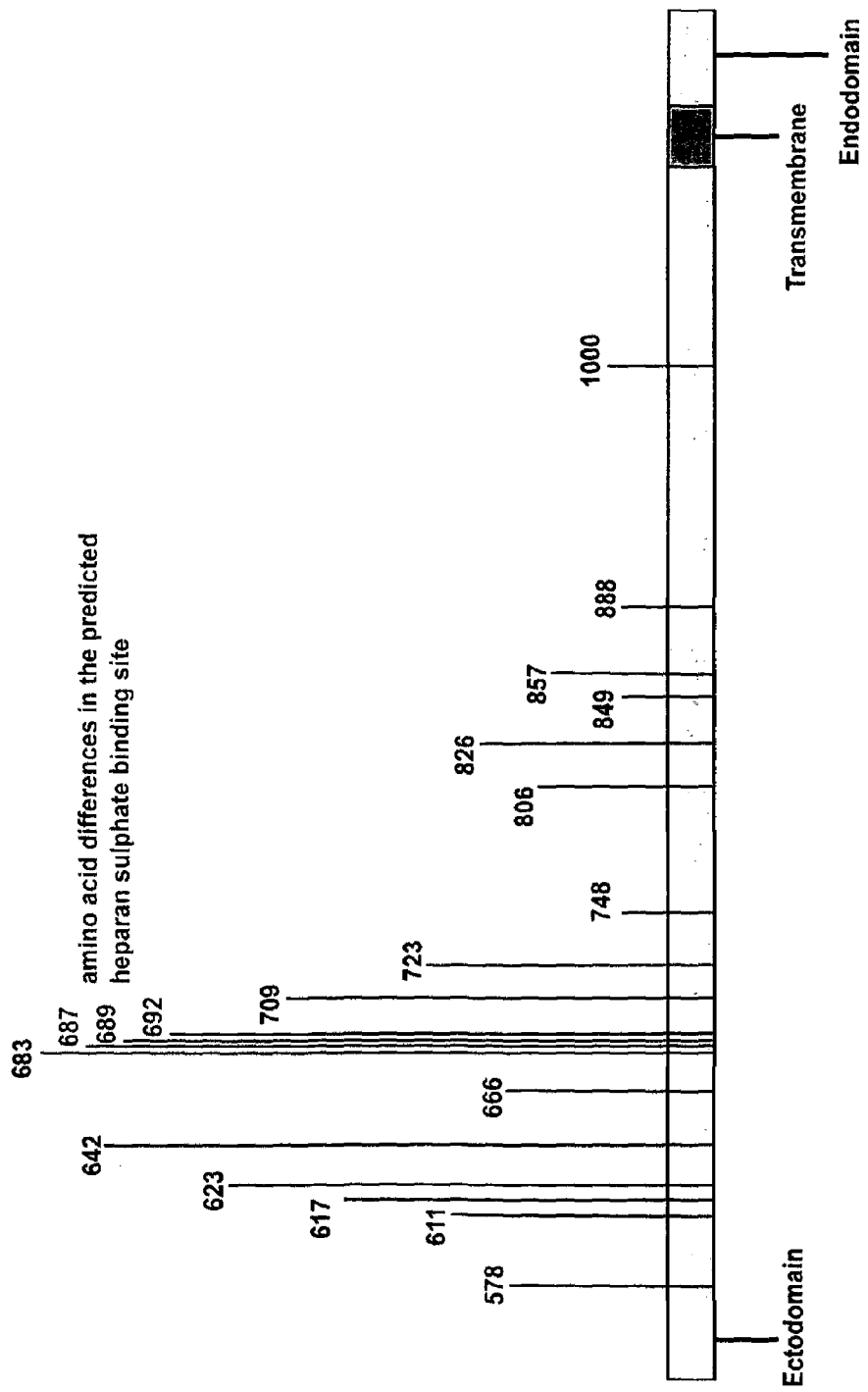

FIG. 14—Amino acid differences between M41 and Beaudette S2 regions.

DETAILED DESCRIPTION

Coronavirus

Coronavirus is a genus of animal virus belonging to the family Coronaviridae. Coronaviruses are enveloped viruses with a positive-sense single-stranded RNA genome and a helical symmetry. The genomic size of coronaviruses ranges from approximately 27 to 32 kilobases, which is the longest size for any known RNA virus.

Coronaviruses primarily infect the upper respiratory and gastrointestinal tract of mammals and birds. Four to five different currently known strains of coronaviruses infect humans. The most publicized human coronavirus, SARS-CoV which causes SARS, has a unique pathogenesis because it causes both upper and lower respiratory tract infections and can also cause gastroenteritis. Coronaviruses are believed to cause a significant percentage of all common colds in human adults. Coronaviruses also cause a range of diseases in farm animals and domesticated pets, some of which can be serious and are a threat to the farming industry. Economically significant coronaviruses of farm animals include infectious bronchitis virus (IBV) which mainly causes respiratory disease in chickens and seriously affects the poultry industry worldwide; porcine coronavirus (transmissible gastroenteritis, TGE) and bovine coronavirus, which both result in diarrhoea in young animals. Feline coronavirus has two forms, feline enteric coronavirus is a pathogen of minor clinical significance, but spontaneous mutation of this virus can result in feline infectious peritonitis (FIP), a disease associated with high mortality. There are also two types of canine coronavirus (CCoV), one that causes mild gastrointestinal disease and one that has been found to cause respiratory disease. Mouse hepatitis virus (MHV) is a coronavirus that causes an epidemic murine illness with high mortality, especially among colonies of laboratory mice. Coronaviruses are divided into three groups, as shown below:

Group 1
Canine coronavirus (CCoV)
Feline coronavirus (FeCoV)

Human coronavirus 229E (HCoV-229E)
Porcine epidemic diarrhoea virus (PEDV)
Transmissible gastroenteritis virus (TGEV)
Human Coronavirus NL63 (NL or New Haven)
Group 2
Bovine coronavirus (BCoV)
Canine respiratory coronavirus (CRCoV)—Common in SE Asia and Micronesia
Human coronavirus OC43 (HCoV-OC43)
Mouse hepatitis virus (MHV)
Porcine haemagglutinating encephalomyelitis virus (HEV)
Rat coronavirus (RCV). Rat Coronavirus is quite prevalent in Eastern Australia where, as of March/April 2008, it has been found among native and feral rodents colonies.
Turkey coronavirus (TCoV)
(No common name as of yet) (HCoV-HKU1)
Severe acute respiratory syndrome coronavirus (SARS-CoV)
Group 3
Infectious bronchitis virus (1BV)
Turkey coronavirus (Bluecomb disease virus)

The virus of the present invention may be a group 1 coronavirus such as TGEV; a group 2 coronavirus such as MHV; or a group 3 coronavirus such as IBV.

IBV

Avian infectious bronchitis (IB) is an acute and highly contagious respiratory disease of chickens which causes significant economic losses. The disease is characterized by respiratory signs including gasping, coughing, sneezing, tracheal rales, and nasal discharge. In young chickens, severe respiratory distress may occur. In layers, respiratory distress, nephritis, decrease in egg production, and loss of internal egg quality and egg shell quality are common.

In broilers, coughing and rattling are common clinical signs, rapidly spreading in all the birds of the premises. Morbidity is 100% in non vaccinated flocks. Mortality varies depending on age, virus strain, and secondary infections but may be up to 60% in non-vaccinated flocks.

The first IBV serotype to be identified was Massachusetts, but in the United States several serotypes, including Arkansas and Delaware, are currently circulating, in addition to the originally identified Massachusetts type.

The IBV strain Beaudette was derived following at least 150 passages in chick embryos. IBV Beaudette is no longer pathogenic for adult birds but rapidly kills embryos.

FIG. 12 and Table 1 shows the amino acid differences between IBV Beaudette and M41.

H120 is a commercial live IBV Massachusetts serotype vaccine strain, attenuated by approximately 120 passages in embryonated chicken eggs. H52 is another Massachusetts strain, and represents an earlier and slightly more pathogenic passage virus (passage 52) during the development of H120. Vaccines based on H120 and H52 are commonly used.

S-Protein

The coronavirus S protein comprises a large, heavily glycosylated ectodomain that can be cleaved during biosynthesis into two subunits (S1 and S2) by a furin-like enzyme in the Golgi apparatus. Not all coronaviruses are cleaved, yet even without cleavage the basic subunit structure of the S protein is conserved. S1 comprises the receptor binding domain (Li et al (2005) Science 309:1864-1868) and S2 comprises the fusion domain. The S protein of IBV is fully cleaved at the S1/S2 boundary, especially in chicken embryo systems.

Figure 1:
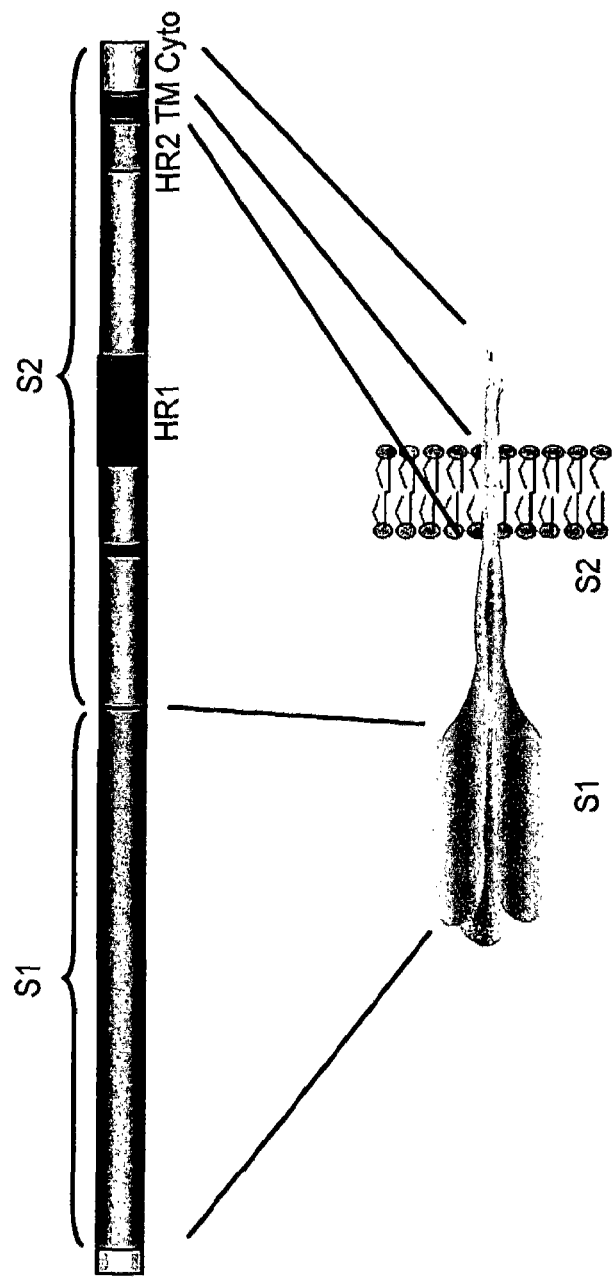
FIG. 1—Schematic diagram of the IBV S protein. The functional S protein is glycosylated and is present as a homotrimer in the virion membrane. The trimeric form of the S1 subunits constitutes the receptor binding domain.

The S2 domain contains five domains or functional regions, as shown in FIG. 1: two domains, HR1 and HR2 form helical structures resulting in the stalk structure of the protein; a transmembrane domain responsible for anchoring the protein to the virion membrane; a cysteine-rich cytoplasmic domain responsible for interacting with other virus structural proteins and a fifth domain, the fusion peptide, responsible for virus-cell fusion or cell-to-cell fusion.

The amino acid differences between M41 and Beaudette S proteins and S2 regions are shown in FIGS. 13 and 14, respectively.

Tissue Tropism

Coronaviruses show strong species and tissue tropism. Likewise, clinical isolates of IBV show distinct tropism both in vivo and in cell culture.

The M41 strain has been adapted for growth on primary chick kidney (CK) cells and is restricted to infection of primary chicken cells, and so needs to be grown on embryonated eggs or CK cells.

The Beaudette strain, on the other hand is known to be able to infect a range of cells in culture, including Vero and baby hamster kidney (BHK) cells.

A coronavirus with restricted tissue tropism is able to infect a smaller number of cell types than a coronavirus with extended tissue tropism.

A coronavirus with restricted tissue tropism, may, for example, be restricted to infection of primary cells, whereas a coronavirus with extended tissue tropism may (in addition to being able to infect primary cells) be able to infect one or more cell lines.

A coronavirus with extended tissue tropism may, for example, have the capacity to infect Vero cells.

The Vero cell lineage was isolated in 1962 from kidney epithelial cells extracted from an African green monkey (*Cercopithecus aethiops*). Vero cells are used for many experimental and clinical purposes, including acting as host cells for growing virus.

The Vero cell lineage is continuous in that it can be replicated through many cycles of division and not become senescent.

The Vero cell lineage has been licensed for use in the manufacture of vaccines and is currently used for the production of polio and rabies vaccines.

The strain with restricted tissue tropism may be immunogenic and capable of inducing a protective or therapeutic immune response in vivo. The strain with restricted tissue tropism may be, for example, a strain currently used for vaccine production. For IBV, this includes strains such as: H52, H120, Ma5, 4/91, D41, D274 and W93. The strain with restricted tissue tropism may be or be derived from an isolate "from the field" such as BJ1, BJ2, or BJ3 (Li and Yang (2001) Avian Pathol 30:535-541).

For IBV, the strain with extended tissue tropism may, for example, be IBV Beaudette, so that the chimaeric protein of the invention comprises all or part of the IBV Beaudette S2 protein.

Cell tropism may be established experimentally by simply challenging a given cell type with infection by a virus. The cytopathic effect (cpe) and the degree of formation of syncytia may then be analysed after a certain number of passages, as described in the Examples. Change in morphology of the infected cells may be analysed using microscopy.

Chimaeric Protein

The present invention relates to a chimaeric coronavirus spike protein (S protein) which is based on an S protein from a coronavirus strain with restricted tissue tropism, but which comprises at least part of the S2 subunit from a coronavirus strain with extended tissue tropism.

The term "based on" indicates that at least the S1 domain is derived or derivable from the strain with restricted tissue tropism. The chimaeric protein may also comprise a part of the S2 domain from the strain with restricted tissue tropism. For example, the transmembrane and/or cytoplasmic domains may be derived or derivable from the strain with restricted tissue tropism.

The chimaeric protein may comprise all or a part of the S2 subunit from the coronavirus strain with extended tissue tropism.

The chimaeric protein may comprise the heparan sulphate binding site located within the S2 subunit of, for example, IBV Beaudette.

A chimaeric infectious bronchitis virus (IBV) S protein may, for example, comprise the sequences XBBXBX (SEQ ID NO: 9) in the part of the S2 protein corresponding to between residues 686 and 691 of the sequence given as SEQ ID No. 1 (FIG. 12A BEAU-CK sequence), where B is a basic residue and X is any amino acid.

For example, the protein may comprise the sequence SRRKRS (SEQ ID NO: 10) or SRRRRS (SEQ ID NO: 11) in the part of the S2 protein corresponding to between residues 686 and 691 of the sequence given as SEQ ID No. 1.

For example, the protein may comprise the sequence SRRKRSLIE (SEQ ID NO: 12) or SRRRRSVIE (SEQ ID NO: 13) in the part of the S2 protein corresponding to between residues 686 and 694 of the sequence given as SEQ ID No. 1.

The chimaeric protein may comprise substantially all of the portion of S2 sequence which is N-terminal to the HR1 domain from the strain with extended tissue tropism. The chimaeric protein may comprise the portion of S2 sequence which is N-terminal to the HR1 domain, together with the HR1 domain from the strain with extended tissue tropism. The chimaeric protein may comprise the portion of S2 sequence which is N-terminal to the HR1 domain, the HR1 domain and the portion of sequence between the HR1 and HR2 domains from the strain with extended tissue tropism. The chimaeric protein may comprise the portion of S2 sequence which is N-terminal to the HR1 domain, the HR1 domain, the portion of sequence between the HR1 and HR2 domains and the HR2 domain from the strain with extended tissue tropism.

The chimaeric protein may comprise substantially all of the S2 subunit from the coronavirus strain with extended tissue tropism.

The chimaeric protein may comprise one or more of the nineteen amino acid changes of the S2 region shown in Table 1 and FIG. 14. In particular the chimaeric protein may comprise an arginine residue at position 687, and a lysine residue at position 689. The chimaeric protein may also comprise a leucine residue at position 692.

The term "substantially all" means that the chimaeric protein comprises at least 95% of the corresponding portion of the wild-type sequence. The missing amino acids may be positioned anywhere within the sequence and may be grouped together (so that a small section of sequence is missing) or separate.

Where a portion of the chimaeric protein is derivable from an S protein for a given strain, that portion may have the same amino acid sequence as the corresponding portion of the wild-type sequence, or it may have one or more amino acid substitutions, additions or deletions compared to the wild-type sequence as long as the original function of that portion of the sequence is retained.

The term "wild type" is used to mean a polypeptide having a primary amino acid sequence which is identical with the native protein (i.e., the viral protein).

A mutant sequence may arise naturally, or may be created artificially (for example by site-directed mutagenesis). The mutant may have at least 70, 80, 90 or 95% sequence identity with the corresponding portion of the wild type sequence. The mutant may have less than 20, 10, or 5 mutations over the corresponding portion of the wild-type sequence.

Identity comparisons can be conducted by eye, or more usually, with the aid of readily available sequence comparison programs. These commercially available computer programs can calculate % identity between two or more sequences. A suitable computer program for carrying out such an alignment is the GCG Wisconsin Bestfit package (University of Wisconsin, U.S.A.; Devereux et al., 1984, Nucleic Acids Research 12:387). Examples of other software that can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nlm.nih.gov).

The sequence may have one or more deletions, insertions or substitutions of amino acid residues which produce a silent change and result in a functionally equivalent molecule. Deliberate amino acid substitutions may be made on the basis of similarity in polarity, charge, solubility, hydrophobicity, hydrophilicity, and/or the amphipathic nature of the residues as long as the activity is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also provides a method for altering the cell tropism of a coronavirus which comprises the step of substitution of at least part of the S2 protein with the S2 protein or corresponding part thereof, from a different strain.

Portions of sequence may be exchanged by methods known in the art, such as by excision and ligation.

By "corresponding part" it is meant that, when the sequence of the S protein of the strain with restricted tissue tropism is aligned with the sequence of the S protein with extended tissue tropism (as shown, for example in FIGS. 12A and 12B) the part of one sequence which aligned with the other.

An alignment between S proteins of different strains is straightforward because coronaviruses share a common domain structure and, between strains, should have a relatively high level of sequence identity. Alignment software may be used such as the BLAST™ package described above.

Nucleotide Sequence

The present invention also provides a nucleotide sequence capable of encoding the chimaeric protein.

The nucleotide sequence may be natural, synthetic or recombinant. It may be double or single stranded, it may be DNA or RNA or combinations thereof. It may, for example, be cDNA, PCR product, genomic sequence or mRNA.

The nucleotide sequence may be codon optimised for production in the host/host cell of choice.

It may be isolated, or as part of a plasmid, virus or host cell.

Plasmid

A plasmid is an extra-chromosomal DNA molecule separate from the chromosomal DNA which is capable of replicating independently of the chromosomal DNA. They are usually circular and double-stranded.

Plasmids, or vectors (as they are sometimes known), may be used to express a protein in a host cell. For example a bacterial host cell may be transfected with a plasmid capable of encoding a particular protein, in order to express that protein. The term also includes yeast artificial chromosomes and bacterial artificial chromosomes which are capable of accommodating longer portions of DNA.

The plasmid of the present invention comprises a nucleotide sequence capable of encoding the chimaeric S gene. It may also comprise one or more additional coronavirus nucleotide sequence(s), or nucleotide sequence(s) capable of encoding one or more other coronavirus proteins such as the replicase gene and/or gene 3.

The plasmid may also comprise a resistance marker, such as the guanine xanthine phosphoribosyltransferase gene (gpt) from *Escherichia coli*, which confers resistance to mycophenolic acid (MPA) in the presence of xanthine and hypoxanthine and is controlled by the vaccinia virus $P_{7.5}$ early/late promoter.

Viral Particle

The present invention also relates to a viral particle with a chimaeric S gene. The viral particle may be a recombinant vaccinia virus (rVV) or a coronavirus.

The viral particle may be recombinant.

The viral particle may be made using a reverse genetics system, such as a vaccinia-virus based reverse genetics system.

In this respect, the present invention also provides a method for making a viral particle by:
 (i) transfecting a plasmid as described in the previous section into a host cell;
 (ii) infecting the host cell with a recombining virus comprising the genome of the coronavirus strain with restricted tissue tropism, minus at least part of the S2 subunit;
 (iii) allowing homologous recombination to occur between the S gene sequences in the plasmid and the corresponding sequences in the recombining virus genome to produce a chimaeric S gene;
 (iv) selecting for recombining virus comprising the chimaeric S gene.

The genome of the coronavirus strain with restricted tissue tropism may lack the part of the S2 protein corresponding to the part provided by the plasmid, so that a chimaeric protein is formed.

The recombining virus is one suitable to allow homologous recombination between its genome and the plasmid. The vaccinia virus is particularly suitable as homologous recombination is routinely used to insert and delete sequences for the vaccinia virus genome.

The above method optionally includes the steps:
 (v) recovery of recombinant coronavirus comprising the chimaeric S gene from the DNA from the recombining virus from step (iv).

Methods for recovering recombinant coronavirus, such as recombinant IBV, are known in the art (See Britton et at (2005) see page 24).

For example, the DNA from the recombining virus from step (iv) may be inserted into a plasmid and used to transfect cells which express cytoplasmic T7 RNA polymerase. (The cells may, for example be pre-infected with a fowlpox virus expressing T7 RNA polymerase). Recombinant coronavirus may then be isolated, for example, from the growth medium.

When the plasmid is inserted into the vaccinia virus genome, an unstable intermediate is formed. Recombinants comprising the plasmid may be selected for e.g. using a resistance marker on the plasmid.

Positive recombinants may then be verified to contain the chimaeric S gene by, for example, PCR and sequencing.

Large stocks of the recombining virus including the chimaeric S gene (e.g. recombinant vaccinia virus, rVV) may be grown up and the DNA extracted in order to carry out step (v).

Suitable reverse genetics systems are known in the art (Casais et al (2001) J. Virol 75:12359-12369; Casais et al (2003) J. Virol. 77:9084-9089; Britton et al (2005) J. Virological Methods 123:203-211; Armesto et al (2008) Methods in Molecular Biology 454:255-273).

Cell

The viral particle may be used to infect a cell.

Since the viral particle comprising the chimaeric S gene has extended tissue tropism, the cell may be derivable from or a part of a cell line.

The cell may, for example, be a baby hamster kidney cell (e.g. BHK-21) or a Vero cell.

The cell may be used to produce the viral particle.

Thus the present invention also provides a method for producing a viral particle which comprises the following steps:
 (i) infection of a cell with a viral particle according to the sixth aspect of the invention;
 (ii) allowing the virus to replicate in the cell; and
 (iii) harvesting the progeny virus.

The cell may be from or part of a cell line, such as a Vero cell. Viral particles may be harvested, for example from the supernatant by methods known in the art, and optionally purified.

The present invention also provides a cell capable of producing a recombinant viral particle according to the fourth aspect of the invention using a reverse genetics system. For example, the cell may comprise a recombining virus genome comprising a nucleotide sequence capable of encoding the chimaeric S gene.

The cell may be able to produce recombinant recombining virus (e.g. vaccinia virus) containing the chimaeric S gene. The cell may be a Vero cell.

Alternatively the cell may be capable of producing recombinant coronavirus by a reverse genetics system. The cell may express or be induced to express T7 polymerase in order to rescue the recombinant viral particle. The cell may be a CK cell.

Vaccine

The viral particle may be used to produce a vaccine.

The vaccine may by a live attenuated form of the viral particle.

The present invention also relates to a method for producing such a vaccine which comprises the step of infecting cells, for example Vero cells, with a viral particle comprising a chimaeric protein according to the first aspect of the invention.

Vaccination Method

The viral particle of the present invention may be used to treat and/or prevent a disease.

To "treat" means to administer the vaccine to a subject having an existing disease in order to lessen, reduce or improve at least one symptom associated with the disease and/or to slow down, reduce or block the progression of the disease.

To "prevent" means to administer the vaccine to a subject who has not yet contracted the disease and/or who is not showing any symptoms of the disease to prevent or impair the cause of the disease (e.g. infection) or to reduce or prevent development of at least one symptom associated with the disease.

The disease may be any disease caused by a coronavirus, such as a respiratory disease and/or gastroenteritis in humans and hepatitis, gastroenteritis, encephalitis, or a respiratory disease in other animals.

The disease may be infectious bronchitis (IB); Porcine epidemic diarrhoea; Transmissible gastroenteritis; Mouse hepatitis virus; Porcine haemagglutinating encephalomyelitis; Severe acute respiratory syndrome (SARS); or Bluecomb disease.

The disease may be infectious bronchitis.

The vaccine may be administered to hatched chicks or chickens, for example by eye drop or intranasal administration. Although accurate, these methods can be expensive e.g. for large broiler flocks. Alternatives include spray inoculation of administration to drinking water but it can be difficult to ensure uniform vaccine application using such methods.

The vaccine may be provided in a form suitable for its administration, such as an eye-dropper for intra-ocular use.

The vaccine may be administered by the in ovo inoculation, for example by injection of embryonated eggs. In ovo vaccination has the advantage that is provides an early stage resistance to the disease. It also facilitates the administration of a uniform dose per subject, unlike spray inoculation and administration via drinking water.

The vaccine may be administered to any suitable compartment of the egg, including allantoic fluid, yolk sac, amnion, air cell or embryo. It may be administered below the shell (aircell) membrane and chorioallantoic membrane.

Usually the vaccine is injected into embryonated eggs during late stages of embryonic development, generally during the final quarter of the incubation period, such as 3-4 days prior to hatch. In chickens, the vaccine may be administered between day 15-19 of the 21-day incubation period, for example at day 17 or 18.

The process can be automated using a robotic injection process, such as those described in WO 2004/078203.

The vaccine may be administered together with one or more other vaccines, for example, vaccines for other diseases, such as Newcastle disease virus (NDV). The present invention also provides a vaccine composition comprising a vaccine according to the invention together with one or more other vaccine(s). The present invention also provides a kit comprising a vaccine according to the invention together with one or more other vaccine(s) for separate, sequential or simultaneous administration.

The vaccine or vaccine composition of the invention may be used to treat a human, animal or avian subject. For example, the subject may be a chick, chicken or mouse (such as a laboratory mouse, e.g. transgenic mouse).

Typically, a physician or veterinarian will determine the actual dosage which will be most suitable for an individual subject or group of subjects and it will vary with the age, weight and response of the particular subject(s).

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as (or in addition to) the carrier, excipient or diluent, any suitable binder(s), lubricant(s), suspending agent(s), coating agent(s), solubilising agent(s), and other carrier agents that may aid or increase the delivery or immunogenicity of the virus.

The invention will now be further described by way of Examples, which are meant to serve to assist one of ordinary skill in the art in carrying out the invention and are not intended in any way to limit the scope of the invention.

EXAMPLES

Example 1

Production of a Chimaeric S Genes Composed of (i) the IBV S1 Subunit from M41 and the S2 Subunit from Beaudette (M1B2); and (ii) the S1 Subunit from Beaudette and the S2 Subunit from M41 (B1M2)

Figure 2:
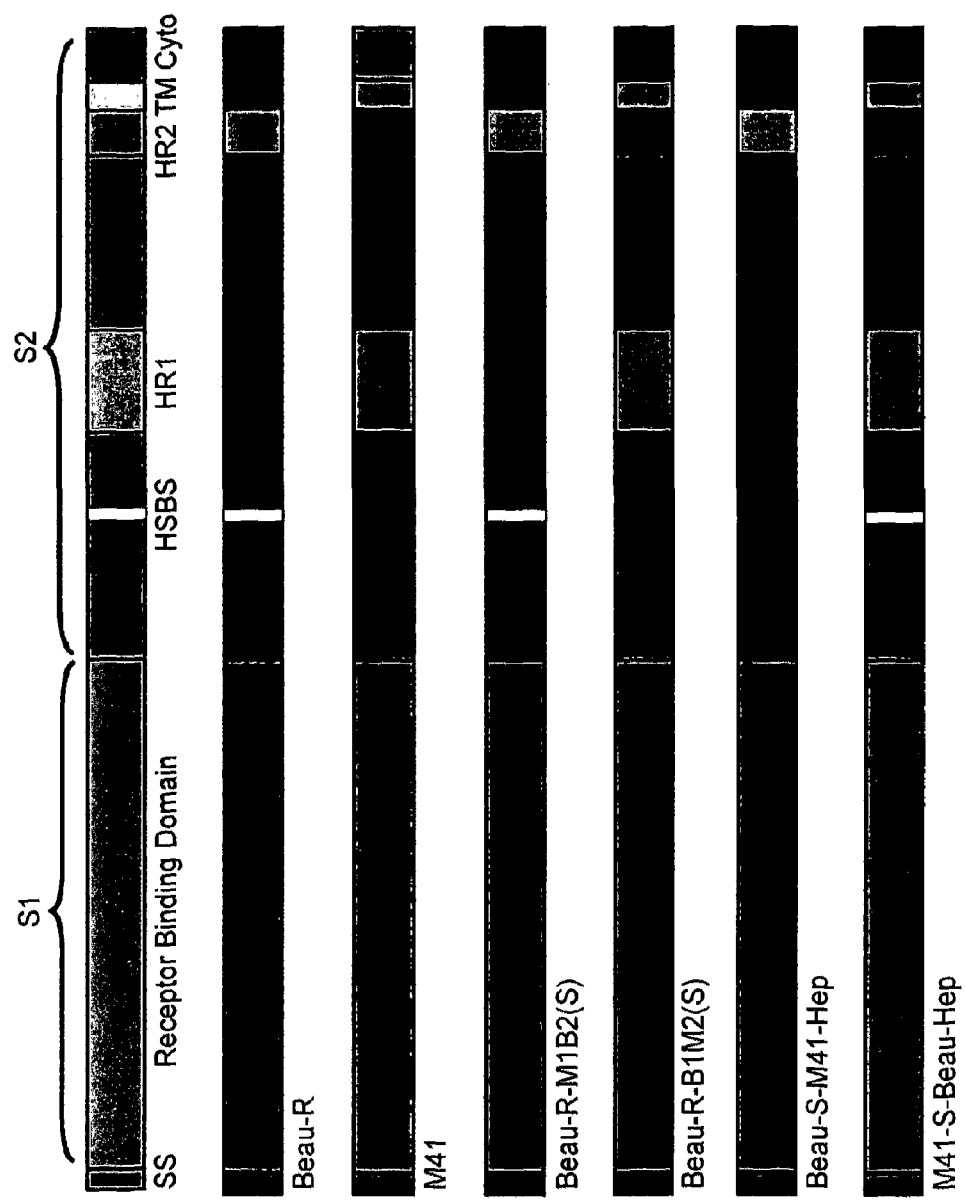
FIG. 2—Schematic diagram showing the S proteins from Beaudette (Beau-R) and M41 and the chimaeric S proteins BeauR-M1B2(S), BeauR-B1M2(S), Beau-S-M41-Hep and M41-S-Beau-Hep. The transmembrane (TM) domain and cytoplasmic (cyto) tail domain of all chimaeric S proteins are derived from the Beaudette S protein. The position of the heparan sulphate-binding site in the S2 subunit is indicted as HSBS.

An overlapping polymerase chain reaction (PCR) strategy was used to create two chimaeric S genes, one with the S1 subunit from M41 and the S2 subunit from Beaudette (M1B2), and the other with the S1 subunit from Beaudette and the S2 subunit from M41 (B1M2; see FIGS. 2 and 3). The S genes of Beau-R (a molecular clone of Beaudette) and M41 are contained within the plasmids pGPT-IBV-StuI-BamHI and pGPT-M41S respectively (see FIG. 4). Primers within the replicase gene and gene 3 were designed close to restriction sites already contained within the IBV genome to make it easier to recover the chimaeric S genes from the plasmids pGPT-S1$_{M41}$S2$_{Beau}$ (M1B2) and pGPT-S1$_{Beau}$S2$_{M41}$ (B1M2). The S gene sequence is identical between Beau-R and M41 at the S1/S2 cleavage site so primers were also designed across this location. Around 500 nucleotides were left either side of the S gene to allow for easy manipulation.

The chimaeric S genes were cloned into plasmids containing the guanine xanthine phosphoribosyltransferase gene (gpt) from *Escherichia coli*, which confers resistance to mycophenolic acid (MPA) in the presence of xanthine and hypoxanthine and is controlled by the vaccinia virus P$_{7.5}$ early/late promoter.

Example 2

Rescue of rIBVs Expressing the Chimaeric S Protein B1M2 or M1B2 and Establishing Whether they can Grow on Vero Cells A vaccinia virus-based reverse genetics system was utilized to create recombinant IBVs (rIBVs) with a chimaeric S gene (see FIG. 5). The plasmids pGPT-S1$_{M41}$S2$_{Beau}$ (M1B2) and pGPT-S1$_{Beau}$S2$_{M41}$ (B1M2) were transfected into Vero cells infected with a recombinant vaccinia virus (rVV) containing the full-length IBV cDNA genome minus the S gene. The plasmid was inserted into the vaccinia virus genome creating an unstable intermediate. Three rounds of plaque purification in the presence of mycophenolic acid, xanthine and hypoxanthine selected gpt-positive recombinants. GPT-negative recombinants were then selected by plaque purification three times in the absence of gpt selection medium.

BeauR-M1B2(S) and BeauR-B1M2(S) recombinants were screened by PCR and sequencing to determine that the chimaeric S gene sequence had been inserted successfully into the rVV genome. Large stocks of the rVV containing the IBV genome with the chimaeric S gene were grown in baby hamster kidney (BHK-21) cells until cytopathic effect (cpe) was observed. The vaccinia virus was purified and the DNA extracted.

Two isolates of rIBV BeauR-M1B2(S) and BeauR-B1M2(S), with the genomic background of Beau-R and the S1 or S2 subunit from M41, were recovered. CK cells infected with recombinant fowlpox virus expressing T7 RNA polymerase (rFPV-T7), were transfected with the rVV DNA and incubated at 37° C. Once ~60% cpe was observed, the culture medium was removed and filtered to remove any rFPV-T7. The culture medium containing the rIBV was passaged three times on CK cells. The total cellular RNA was isolated and analysed for the presence of IBV RNA by RT-PCR. The S gene was sequenced.

After three passages on CK cells, rIBV BeauR-M1B2(S) and BeauR-B1M2(S) were passaged three times on Vero cells. Photographs of rIBV BeauR-M1B2(S) and BeauR-B1M2(S)-infected Vero cells have been taken by brightfield microscopy (FIG. 6) and by confocal microscopy with immunofluorescence (FIG. 7). The recombinant viruses were titrated on CK cells and the growth kinetics on Vero cells investigated (FIG. 8).

BeauR-B1M2(S) formed no cpe on Vero cells and very few infected Vero cells were observed by confocal microscopy with indirect immunofluorescence. The growth curve indicates that BeauR-B1M2(S) is unable to replicate on Vero cells. BeauR-M1B2(S) caused extensive cpe on Vero cells after one passage and was further passaged on Vero cells to passage 7, forming syncytia from passage 5. The growth curve indicates that BeauR-M1B2(S) is able to replicate on Vero cells.

As shown in FIGS. 6-8, Vero cells do not support the growth of M41, BeauR-M41(S), the rIBV derived from Beaudette but expressing the M41 S protein, or BeauR-B1M2(S), the morphology of the cells infected with these strains of IBV is similar to mock infected cells. However, the Vero cells infected with BeauR-M1B2(S) show the same morphology as those infected with Beaudette (Beau-R). These results indicate that the S2 subunit is involved in the infectivity of Vero cells.

Example 3

Soluble Heparin is Able to Block the Infection of Vero Cells Using rIBVs Beau-R and BeauR-M1B2(S)

Plaque reduction assays were carried out in which Beau-R and the two BeauR-M41(S1) isolates have been incubated in the presence of soluble heparin sodium salt at various concentrations 0-20 mg/ml before carrying out plaque assays on Vero cells. The number of plaques produced has been analysed to find out whether the presence of heparin has any effect on the ability of the viruses to grow on Vero cells (FIG. 9).

Beau-R and the two BeauR-M1B2(S) isolates have been incubated in the presence of heparin sodium salt at 15 mg/ml and in absence before infecting Vero cells. Confocal microscopy and indirect immunofluorescence was used to observe the effect of heparin on the number of infected cells present (FIG. 10). Ten fields of vision per sample were analysed by confocal microscopy at ×40 magnification and the percentage of infected cells was calculated.

FIG. 9 shows a plaque reduction assay on Vero cells of IBV pre-treated with increasing amounts of soluble heparin. The green line represents Beaudette and the blue and red lines represent the two rIBV expressing the chimaeric M1B2 S protein. FIG. 10 shows a bar chart comparing the effect of soluble heparin on the percentage of IBV-infected Vero cells, measured by confocal microscopy with indirect immunofluorescence. These results indicate that soluble heparin has the same effect, the blocking of infection, on the rIBVs as on Beaudette.

Example 4

Introduction of the Heparan Sulphate Binding Site into the S2 Subunit of the M41 S gene in BeauR-M41(S) and Replacement of the Heparan Sulphate Binding Site in the S Protein of Beau-R with the Corresponding Region from the M41 S Protein Two plasmids have been designed, one with a section of the Beau-R S gene with the heparan sulphate binding site located with the S2 subunit swapped for the corresponding sequence of M41 (Beau-S-M41-Hep), and the other with a section of the M41 S gene with the heparan sulphate binding site from Beau-R (M41-S-Beau-Hep). Both plasmids contain the gpt gene for selection.

The reverse genetics system as described in example 2 and FIG. 5 has been used to create two chimaeric rIBVs, Beau-S-M41-Hep and M41-S-Beau-Hep (FIGS. 2 and 11). Two suitable recombinants of each were passaged three times on CK cells then their growth characteristics on Vero cells analysed by brightfield microscopy to assess whether the rIBVs cause cpe (FIG. 6), confocal microscopy of infected cells (FIG. 7) and growth kinetics (FIG. 8).

As shown in FIGS. 6-8, Vero cells do not support the growth of M41, BeauR-M41(S), BeauR-B1M2(S) or Beau-S-M41-Hep. The morphology of the cells infected with these strains of IBV is similar to mock infected cells and very few infected cells were observed by confocal microscopy with indirect immunofluorescence. However, the Vero cells infected with M41-S-Beau-Hep show the same morphology as those infected with Beaudette (Beau-R) and BeauR-M1B2(S). Growth curves on Vero cells showed that removing the heparan sulphate binding site from Beau-R removed its ability to grow on Vero cells and introducing the heparan sulphate binding site into the BeauR-M41(S) S protein allowed growth on Vero cells. These results indicate that the heparan sulphate binding site within the S2 subunit of Beaudette is involved in the infectivity of Vero cells.

Throughout this specification, unless the context requires otherwise, the word "comprise", or variations such as "comprises" or "comprising", should be understood to imply the inclusion of a stated element or integer or group of elements or integers but not the exclusion of any other element or integer or groups of elements or integers.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, virology or related fields are intended to be within the scope of the following claims.

The invention claimed is:

1. A chimaeric infectious bronchitis virus (IBV) S protein that comprises the S1 domain of an IBV strain with restricted tropism that is unable to grow on a cell line, and comprises at least part of the S2 domain from an IBV strain with extended tropism that is able to grow on said cell line, such that an IBV comprising the chimaeric S protein is able to grow on said cell line.

2. The chimaeric S protein according to claim 1, which comprises at least 95% of the sequence of the S2 domain of the IBV strain with extended tropism.

3. The chimaeric S protein according to claim 1, wherein said cell line is Vero.

4. The chimaeric S protein according to claim 1, which comprises the sequences XBBXBX (SEQ ID NO: 9) in the part of the S2 protein corresponding to residues 686 to 691 of SEQ ID NO: 1, where B is a basic residue and X is any amino acid.

5. The chimaeric S protein according to claim 4, which comprises the sequence SRRKRS (SEQ ID NO: 10) or SRRRRS (SEQ ID NO: 11) in the part of the S2 protein corresponding to residues 686 to 691 of SEQ ID NO: 1.

6. The chimaeric S protein according to claim 5, which comprises the sequence SRRKRSLIE (SEQ ID NO: 12) or SRRRRSVIE (SEQ ID NO: 13) in the part of the S2 protein corresponding to residues 686 to 694 of SEQ ID NO: 1.

7. The chimaeric S protein according to claim 1, wherein the IBV strain which is capable of growing on a cell line is IBV Beaudette.

8. An isolated nucleic acid comprising a nucleotide sequence encoding a chimaeric S protein, wherein the chimaeric S protein comprises the S1 domain of an IBV strain with restricted tropism that is unable to grow on a cell line, and comprises at least part of the S2 domain from an IBV strain with extended tropism that is able to grow on said cell line, such that an IBV comprising the chimaeric S protein is able to grow on said cell line.

9. A plasmid comprising a nucleic acid according to claim 8.

10. An infectious bronchitis virus comprising a chimaeric S protein and/or a nucleotide sequence that encodes the chimaeric S protein, wherein the chimeric S protein comprises the S1 domain of an IBV strain with restricted tropism that is unable to grow on a cell line, and comprises at least part of the S2 domain from an IBV strain with extended tropism that is able to grow on said cell line, such that an IBV comprising the chimaeric S protein is able to grow on said cell line.

11. An infectious bronchitis virus according to claim 10, which is able to grow on Vero cells.

12. An infectious bronchitis virus according to claim 11, whose infection of Vero cells is blocked by soluble heparin.

13. A method for making a recombining virus encoding an infectious bronchitis virus comprising a chimaeric S protein, comprising:
(i) transfecting a plasmid according to claim 9 into a host cell;
(ii) infecting the host cell with a recombining virus comprising a DNA sequence encoding the genome of the IBV strain with restricted tissue tropism, lacking at least part of the S2 subunit;
(iii) allowing homologous recombination to occur between the S gene sequences in the plasmid and the corresponding sequences in the recombining virus genome to produce a chimaeric S gene; and
(iv) selecting for recombining virus comprising the chimaeric S gene, wherein the chimaeric S gene comprises a nucleotide sequence that encodes a chimaeric S protein, wherein the chimaeric S protein comprises the S1 domain of an IBV strain with restricted tropism that is unable to grow on a cell line, and comprises at least part of the S2 domain from an IBV strain with extended tropism that is able to grow on said cell line, such that an IBV comprising the chimaeric S protein is able to grow on said cell line.

14. The method according to claim 13, wherein the recombining virus is a vaccinia virus.

15. The method according to claim 13 which further comprises:
(v) recovering recombinant IBV comprising the chimaeric S gene from the DNA from the recombining virus from step (iv).

16. An isolated cell transfected with a plasmid according to claim 9 or infected with the virus of claim 11.

17. A cell according to claim 16 that is a Vero cell.

18. A composition comprising an infectious bronchitis virus according to claim 10 and a pharmaceutically acceptable diluent, adjuvant, excipient, or carrier.

19. A vaccine comprising an infectious bronchitis virus according to claim 10.

20. A method for treating and/or preventing IBV in a subject which comprises the step of administering a vaccine according to claim 19 to the subject.

21. A method for producing a vaccine comprising infecting Vero cells with the infectious bronchitis virus according to claim 11 and producing a vaccine from virus grown in the infected Vero cells.

* * * * *

SEQUENCE LISTING

<160> NUMBER OF SEQ ID NOS: 13

<210> SEQ ID NO 1
<211> LENGTH: 1162
<212> TYPE: PRT
<213> ORGANISM: Infectious bronchitis virus

<400> SEQUENCE: 1

```
Met Leu Val Thr Pro Leu Leu Val Thr Leu Leu Cys Ala Leu Cys
1               5                   10                  15

Ser Ala Val Leu Tyr Asp Ser Ser Tyr Val Tyr Tyr Gln Ser
            20                  25                  30

Ala Phe Arg Pro Pro Ser Gly Trp His Leu Gln Gly Gly Ala Tyr Ala
            35                  40                  45

Val Val Asn Ile Ser Ser Glu Phe Asn Asn Ala Gly Ser Ser Ser Gly
        50                  55                  60

Cys Thr Val Gly Ile Ile His Gly Gly Arg Val Val Asn Ala Ser Ser
65                  70                  75                  80

Ile Ala Met Thr Ala Pro Ser Ser Gly Met Ala Trp Ser Ser Ser Gln
                85                  90                  95

Phe Cys Thr Ala His Cys Asn Phe Ser Asp Thr Thr Val Phe Val Thr
                    100                 105                 110

His Cys Tyr Lys His Gly Gly Cys Pro Leu Thr Gly Met Leu Gln Gln
                115                 120                 125

Asn Leu Ile Arg Val Ser Ala Met Lys Asn Gly Gln Leu Phe Tyr Asn
            130                 135                 140

Leu Thr Val Ser Val Ala Lys Tyr Pro Thr Phe Arg Ser Phe Gln Cys
145                 150                 155                 160

Val Asn Asn Leu Thr Ser Val Tyr Leu Asn Gly Asp Leu Val Tyr Thr
                165                 170                 175

Ser Asn Glu Thr Ile Asp Val Thr Ser Ala Gly Val Tyr Phe Lys Ala
                180                 185                 190

Gly Gly Pro Ile Thr Tyr Lys Val Met Arg Glu Val Lys Ala Leu Ala
            195                 200                 205

Tyr Phe Val Asn Gly Thr Ala Gln Asp Val Ile Leu Cys Asp Gly Ser
        210                 215                 220

Pro Arg Gly Leu Leu Ala Cys Gln Tyr Asn Thr Gly Asn Phe Ser Asp
225                 230                 235                 240

Gly Phe Tyr Pro Phe Thr Asn Ser Ser Leu Val Lys Gln Lys Phe Ile
                245                 250                 255

Val Tyr Arg Glu Asn Ser Val Asn Thr Thr Cys Thr Leu His Asn Phe
                260                 265                 270

Ile Phe His Asn Glu Thr Gly Ala Asn Pro Asn Pro Ser Gly Val Gln
            275                 280                 285

Asn Ile Gln Thr Tyr Gln Thr Lys Thr Ala Gln Ser Gly Tyr Tyr Asn
        290                 295                 300

Phe Asn Phe Ser Phe Leu Ser Ser Phe Val Tyr Lys Glu Ser Asn Phe
305                 310                 315                 320

Met Tyr Gly Ser Tyr His Pro Ser Cys Lys Phe Arg Leu Glu Thr Ile
                325                 330                 335

Asn Asn Gly Leu Trp Phe Asn Ser Leu Ser Val Ser Ile Ala Tyr Gly
            340                 345                 350

Pro Leu Gln Gly Gly Cys Lys Gln Ser Val Phe Lys Gly Arg Ala Thr
        355                 360                 365
```

```
Cys Cys Tyr Ala Tyr Ser Tyr Gly Gly Pro Ser Leu Cys Lys Gly Val
    370                 375                 380

Tyr Ser Gly Glu Leu Asp His Asn Phe Glu Cys Gly Leu Leu Val Tyr
385                 390                 395                 400

Val Thr Lys Ser Gly Gly Ser Arg Ile Gln Thr Ala Thr Glu Pro Pro
                405                 410                 415

Val Ile Thr Gln Asn Asn Tyr Asn Asn Ile Thr Leu Asn Thr Cys Val
                420                 425                 430

Asp Tyr Asn Ile Tyr Gly Arg Thr Gly Gln Gly Phe Ile Thr Asn Val
            435                 440                 445

Thr Asp Ser Ala Val Ser Tyr Asn Tyr Leu Ala Asp Ala Gly Leu Ala
450                 455                 460

Ile Leu Asp Thr Ser Gly Ser Ile Asp Ile Phe Val Val Gln Gly Glu
465                 470                 475                 480

Tyr Gly Leu Asn Tyr Tyr Lys Val Asn Pro Cys Glu Asp Val Asn Gln
                485                 490                 495

Gln Phe Val Val Ser Gly Gly Lys Leu Val Gly Ile Leu Thr Ser Arg
            500                 505                 510

Asn Glu Thr Gly Ser Gln Leu Leu Glu Asn Gln Phe Tyr Ile Lys Ile
            515                 520                 525

Thr Asn Gly Thr Arg Arg Phe Arg Arg Ser Ile Thr Glu Asn Val Ala
530                 535                 540

Asn Cys Pro Tyr Val Ser Tyr Gly Lys Phe Cys Ile Lys Pro Asp Gly
545                 550                 555                 560

Ser Ile Ala Thr Ile Val Pro Lys Gln Leu Glu Gln Phe Val Ala Pro
                565                 570                 575

Leu Phe Asn Val Thr Glu Asn Val Leu Ile Pro Asn Ser Phe Asn Leu
            580                 585                 590

Thr Val Thr Asp Glu Tyr Ile Gln Thr Arg Met Asp Lys Val Gln Ile
            595                 600                 605

Asn Cys Leu Gln Tyr Val Cys Gly Ser Ser Leu Asp Cys Arg Lys Leu
610                 615                 620

Phe Gln Gln Tyr Gly Pro Val Cys Asp Asn Ile Leu Ser Val Val Asn
625                 630                 635                 640

Ser Val Gly Gln Lys Glu Asp Met Glu Leu Leu Asn Phe Tyr Ser Ser
                645                 650                 655

Thr Lys Pro Ala Gly Phe Asn Thr Pro Val Leu Ser Asn Val Ser Thr
                660                 665                 670

Gly Glu Phe Asn Ile Ser Leu Leu Leu Thr Asn Pro Ser Ser Arg Arg
            675                 680                 685

Lys Arg Ser Leu Ile Glu Asp Leu Leu Phe Thr Ser Val Glu Ser Val
690                 695                 700

Gly Leu Pro Thr Asn Asp Ala Tyr Lys Asn Cys Thr Ala Gly Pro Leu
705                 710                 715                 720

Gly Phe Phe Lys Asp Leu Ala Cys Ala Arg Glu Tyr Asn Gly Leu Leu
                725                 730                 735

Val Leu Pro Pro Ile Ile Thr Ala Glu Met Gln Ala Leu Tyr Thr Ser
                740                 745                 750

Ser Leu Val Ala Ser Met Ala Phe Gly Gly Ile Thr Ala Ala Gly Ala
            755                 760                 765

Ile Pro Phe Ala Thr Gln Leu Gln Ala Arg Ile Asn His Leu Gly Ile
770                 775                 780

Thr Gln Ser Leu Leu Leu Lys Asn Gln Glu Lys Ile Ala Ala Ser Phe
```

-continued

```
            785                 790                 795                 800
Asn Lys Ala Ile Gly His Met Gln Glu Gly Phe Arg Ser Thr Ser Leu
                805                 810                 815

Ala Leu Gln Gln Ile Gln Asp Val Val Ser Lys Gln Ser Ala Ile Leu
                820                 825                 830

Thr Glu Thr Met Ala Ser Leu Asn Lys Asn Phe Gly Ala Ile Ser Ser
                835                 840                 845

Val Ile Gln Glu Ile Tyr Gln Gln Phe Asp Ala Ile Gln Ala Asn Ala
    850                 855                 860

Gln Val Asp Arg Leu Ile Thr Gly Arg Leu Ser Ser Leu Ser Val Leu
865                 870                 875                 880

Ala Ser Ala Lys Gln Ala Glu Tyr Ile Arg Val Ser Gln Gln Arg Glu
                885                 890                 895

Leu Ala Thr Gln Lys Ile Asn Glu Cys Val Lys Ser Gln Ser Ile Arg
                900                 905                 910

Tyr Ser Phe Cys Gly Asn Gly Arg His Val Leu Thr Ile Pro Gln Asn
                915                 920                 925

Ala Pro Asn Gly Ile Val Phe Ile His Phe Ser Tyr Thr Pro Asp Ser
    930                 935                 940

Phe Val Asn Val Thr Ala Ile Val Gly Phe Cys Val Lys Pro Ala Asn
945                 950                 955                 960

Ala Ser Gln Tyr Ala Ile Val Pro Ala Asn Gly Arg Gly Ile Phe Ile
                965                 970                 975

Gln Val Asn Gly Ser Tyr Tyr Ile Thr Ala Arg Asp Met Tyr Met Pro
                980                 985                 990

Arg Ala Ile Thr Ala Gly Asp Val Val Thr Leu Thr Ser Cys Gln Ala
        995                 1000                1005

Asn Tyr Val Ser Val Asn Lys Thr Val Ile Thr Thr Phe Val Asp
        1010                1015                1020

Asn Asp Asp Phe Asp Phe Asn Asp Glu Leu Ser Lys Trp Trp Asn
        1025                1030                1035

Asp Thr Lys His Glu Leu Pro Asp Phe Asp Lys Phe Asn Tyr Thr
        1040                1045                1050

Val Pro Ile Leu Asp Ile Asp Ser Glu Ile Asp Arg Ile Gln Gly
        1055                1060                1065

Val Ile Gln Gly Leu Asn Asp Ser Leu Ile Asp Leu Glu Lys Leu
        1070                1075                1080

Ser Ile Leu Lys Thr Tyr Ile Lys Trp Pro Trp Tyr Val Trp Leu
        1085                1090                1095

Ala Ile Ala Phe Ala Thr Ile Ile Phe Ile Leu Ile Leu Gly Trp
        1100                1105                1110

Val Phe Phe Met Thr Gly Cys Cys Gly Cys Cys Cys Gly Cys Phe
        1115                1120                1125

Gly Ile Met Pro Leu Met Ser Lys Cys Gly Lys Lys Ser Ser Tyr
        1130                1135                1140

Tyr Thr Thr Phe Asp Asn Asp Val Val Thr Glu Gln Tyr Arg Pro
        1145                1150                1155

Lys Lys Ser Val
        1160

<210> SEQ ID NO 2
<211> LENGTH: 900
<212> TYPE: DNA
<213> ORGANISM: Infectious bronchitis virus
```

<400> SEQUENCE: 2

```
ctgaaaatgt tgcaaattgc ccttatgtta gttatggtaa gttttgtata aaacctgatg      60
gctcaattgc cacaatagta ccaaaacaat tggaacagtt tgtggcacct ttatttaatg     120
ttactgaaaa tgtgctcata cctaacagtt tcaacttaac tgttacagat gagtacatac     180
aaacgcgtat ggataaggtc caaattaatt gcctgcagta tgtttgtggc agttctctgg     240
attgtagaaa gttgtttcaa caatatgggc ctgtttgcga caacatattg tctgtagtaa     300
atagtgttgg tcaaaaagaa gatatggaac ttttgaattt ctattcttct actaaaccgg     360
ctggttttaa tacaccagtt cttagtaatg ttagcactgg tgagtttaat atttctcttc     420
tgttaacaaa tcctagtagt cgtagaaagc gttctcttat tgaagacctt ctatttacaa     480
gcgttgaatc tgttggacta ccaacaaatg acgcatataa aaattgcact gcaggacctt     540
taggcttttt taaggacctt gcgtgtgctc gtgaatataa tggtttgctt gtgttgcctc     600
ctatcataac agcagaaatg caagctttgt atactagttc tctagtagct tctatggctt     660
ttggtggtat tactgcagct ggtgctatac cttttgccac acaactgcag gctagaatta     720
atcacttggg tattacccag tcactttttgt tgaagaatca agaaaaaatt gctgcttcct     780
ttaataaggc cattggtcat atgcaggaag gttttagaag tacatctcta gcattacaac     840
aaattcaaga tgttgttagt aaacagagtg ctattcttac tgagactatg gcatcactta     900
```

<210> SEQ ID NO 3
<211> LENGTH: 900
<212> TYPE: DNA
<213> ORGANISM: Artificial Sequence
<220> FEATURE:
<223> OTHER INFORMATION: Chimaeric rIBV

<400> SEQUENCE: 3

```
ctgaaaatgt tgcaaattgc ccttatgtta gttatggtaa gttttgtata aaacctgatg      60
gctcaattgc cacaatagta ccaaaacaat tggaacagtt tgtggcacct ttatttaatg     120
ttactgaaaa tgtgctcata cctaacagtt tcaacttaac tgttacagat gagtacatac     180
aaacgcgtat ggataaggtc caaattaatt gcctgcagta tgtttgtggc agttctctgg     240
attgtagaaa gttgtttcaa caatatgggc ctgtttgcga caacatattg tctgtagtaa     300
atagtgttgg tcaaaaagaa gatatggaac ttttgaattt ctattcttct actaaaccgg     360
ctggttttaa tacaccagtt cttagtaatg ttagcactgg tgagtttaat atttctcttc     420
tgttaacaaa tcctagtagt cctagaaggc gttcttttat tgaagacctt ctatttacaa     480
gcgttgaatc tgttggacta ccaacaaatg acgcatataa aaattgcact gcaggacctt     540
taggcttttt taaggacctt gcgtgtgctc gtgaatataa tggtttgctt gtgttgcctc     600
ctatcataac agcagaaatg caagctttgt atactagttc tctagtagct tctatggctt     660
ttggtggtat tactgcagct ggtgctatac cttttgccac acaactgcag gctagaatta     720
atcacttggg tattacccag tcactttttgt tgaagaatca agaaaaaatt gctgcttcct     780
ttaataaggc cattggtcat atgcaggaag gttttagaag tacatctcta gcattacaac     840
aaattcaaga tgttgttagt aaacagagtg ctattcttac tgagactatg gcatcactta     900
```

<210> SEQ ID NO 4
<211> LENGTH: 900
<212> TYPE: DNA
<213> ORGANISM: Artificial Sequence
<220> FEATURE:

<223> OTHER INFORMATION: Chimaeric rIBV

<400> SEQUENCE: 4

```
ctgaaaatgt tgcaaattgc ccttatgtta gttatggtaa gttttgtata aaacctgatg      60
gttcaattgc cacaatagta ccaaaacaat tggaacagtt tgtggcacct ttacttaatg     120
ttactgaaaa tgtgctcata cctaacagtt ttaatttaac tgttacagat gagtacatac     180
aaacgcgtat ggataaggtc caaattaatt gtctgcagta tgtttgtggc aattctctgg     240
attgtagaga tttgtttcaa caatatgggc ctgtttgtga caacatattg tctgtagtaa     300
atagtattgg tcaaaaagaa gatatggaac ttttgaattt ctattcttct actaaaccgg     360
ctggttttaa tacaccattt cttagtaatg ttagcactgg tgagtttaat atttctcttc     420
tgttaacaac tcctagtagt cgtagaaagc gttctcttat tgaagaccct ctatttacaa     480
gcgttgaatc tgttggatta ccaacagatg acgcatacaa aaattgcact gcaggacctt     540
taggttttct taaggacctt gcgtgtgctc gtgaatataa tggtttgctt gtgttgcctc     600
ccattataac agcagaaatg caaactttgt atactagttc tctagtagct tctatggctt     660
ttggtggtat tactgcagct ggtgctatac cttttgccac acaactgcag gctagaatta     720
atcacttggg tattacccag tcacttttgt tgaagaatca agaaaaaatt gctgcttcct     780
taataaggc cattggtcgt atgcaggaag ttttagaag tacatctcta gcattacaac      840
aaattcaaga tgttgttaat aagcagagtg ctattcttac tgagactatg gcatcactta     900
```

<210> SEQ ID NO 5
<211> LENGTH: 900
<212> TYPE: DNA
<213> ORGANISM: Infectious bronchitis virus

<400> SEQUENCE: 5

```
ctgaaaatgt tgcaaattgc ccttatgtta gttatggtaa gttttgtata aaacctgatg      60
gttcaattgc cacaatagta ccaaaacaat tggaacagtt tgtggcacct ttacttaatg     120
ttactgaaaa tgtgctcata cctaacagtt ttaatttaac tgttacagat gagtacatac     180
aaacgcgtat ggataaggtc caaattaatt gtctgcagta tgtttgtggc aattctctgg     240
attgtagaga tttgtttcaa caatatgggc ctgtttgtga caacatattg tctgtagtaa     300
atagtattgg tcaaaaagaa gatatggaac ttttgaattt ctattcttct actaaaccgg     360
ctggttttaa tacaccattt cttagtaatg ttagcactgg tgagtttaat atttctcttc     420
tgttaacaac tcctagtagt cctagaaggc gttcttttat tgaagaccct ctatttacaa     480
gcgttgaatc tgttggatta ccaacagatg acgcatacaa aaattgcact gcaggacctt     540
taggttttct taaggacctt gcgtgtgctc gtgaatataa tggtttgctt gtgttgcctc     600
ccattataac agcagaaatg caaactttgt atactagttc tctagtagct tctatggctt     660
ttggtggtat tactgcagct ggtgctatac cttttgccac acaactgcag gctagaatta     720
atcacttggg tattacccag tcacttttgt tgaagaatca agaaaaaatt gctgcttcct     780
taataaggc cattggtcgt atgcaggaag ttttagaag tacatctcta gcattacaac      840
aaattcaaga tgttgttaat aagcagagtg ctattcttac tgagactatg gcatcactta     900
```

<210> SEQ ID NO 6
<211> LENGTH: 1153
<212> TYPE: PRT
<213> ORGANISM: Infectious bronchitis virus

<400> SEQUENCE: 6

-continued

```
Met Leu Val Thr Pro Leu Leu Val Thr Leu Leu Cys Val Leu Cys
 1               5                  10                  15

Ser Ala Ala Leu Tyr Asp Ser Ser Tyr Val Tyr Tyr Gln Ser
            20                  25                  30

Ala Phe Arg Pro Pro Asn Gly Trp His Leu His Gly Ala Tyr Ala
        35                  40                  45

Val Val Asn Ile Ser Ser Glu Ser Asn Ala Gly Ser Ser Pro Gly
    50                  55                  60

Cys Ile Val Gly Thr Ile His Gly Gly Arg Val Val Asn Ala Ser Ser
 65                  70                  75                  80

Ile Ala Met Thr Ala Pro Ser Ser Gly Met Ala Trp Ser Ser Gln
                85                  90                  95

Phe Cys Thr Ala His Cys Asn Phe Ser Asp Thr Thr Val Phe Val Thr
               100                 105                 110

His Cys Tyr Lys Tyr Asp Gly Cys Pro Ile Thr Gly Met Leu Gln Lys
               115                 120                 125

Asn Phe Leu Arg Val Ser Ala Met Lys Asn Gly Gln Leu Phe Tyr Asn
    130                 135                 140

Leu Thr Val Ser Val Ala Lys Tyr Pro Thr Phe Lys Ser Phe Gln Cys
145                 150                 155                 160

Val Asn Asn Leu Thr Ser Val Tyr Leu Asn Gly Asp Leu Val Tyr Thr
                165                 170                 175

Ser Asn Glu Thr Thr Asp Val Thr Ser Ala Gly Val Tyr Phe Lys Ala
                180                 185                 190

Gly Gly Pro Ile Thr Tyr Lys Val Met Arg Glu Val Lys Ala Leu Ala
                195                 200                 205

Tyr Phe Val Asn Gly Thr Ala Gln Asp Val Ile Leu Cys Asp Gly Ser
    210                 215                 220

Pro Arg Gly Leu Leu Ala Cys Gln Tyr Asn Thr Gly Asn Phe Ser Asp
225                 230                 235                 240

Gly Phe Tyr Pro Phe Ile Asn Ser Ser Leu Val Lys Gln Lys Phe Ile
                245                 250                 255

Val Tyr Arg Glu Asn Ser Val Asn Thr Thr Phe Thr Leu His Asn Phe
                260                 265                 270

Thr Phe His Asn Glu Thr Gly Ala Asn Pro Asn Pro Ser Gly Val Gln
                275                 280                 285

Asn Ile Gln Thr Tyr Gln Thr Gln Thr Ala Gln Ser Gly Tyr Tyr Asn
    290                 295                 300

Phe Asn Phe Ser Phe Leu Ser Ser Phe Val Tyr Lys Glu Ser Asn Phe
305                 310                 315                 320

Met Tyr Gly Ser Tyr His Pro Ser Cys Asn Phe Arg Leu Glu Thr Ile
                325                 330                 335

Asn Asn Gly Leu Trp Phe Asn Ser Leu Ser Val Ser Ile Ala Tyr Gly
                340                 345                 350

Pro Leu Gln Gly Gly Cys Lys Gln Ser Val Phe Ser Gly Arg Ala Thr
                355                 360                 365

Cys Cys Tyr Ala Tyr Ser Tyr Gly Gly Pro Ser Leu Cys Lys Gly Val
                370                 375                 380

Tyr Ser Gly Glu Leu Asp Leu Asn Phe Glu Cys Gly Leu Leu Val Tyr
385                 390                 395                 400

Val Thr Lys Ser Gly Gly Ser Arg Ile Gln Thr Ala Thr Glu Pro Pro
                405                 410                 415
```

```
Val Ile Thr Arg His Asn Tyr Asn Asn Ile Thr Leu Asn Thr Cys Val
            420                 425                 430

Asp Tyr Asn Ile Tyr Gly Arg Thr Gly Gln Gly Phe Ile Thr Asn Val
            435                 440                 445

Thr Asp Ser Ala Val Ser Tyr Asn Tyr Leu Ala Asp Ala Gly Leu Ala
            450                 455                 460

Ile Leu Asp Thr Ser Gly Ser Ile Asp Ile Phe Val Val Gln Gly Glu
465                 470                 475                 480

Tyr Gly Leu Thr Tyr Tyr Lys Val Tyr Pro Cys Glu Asp Val Asn Gln
                485                 490                 495

Gln Phe Val Val Ser Gly Gly Lys Leu Val Gly Ile Leu Thr Ser Arg
            500                 505                 510

Asn Glu Thr Gly Ser Gln Leu Leu Glu Asn Gln Phe Tyr Ile Lys Ile
            515                 520                 525

Thr Asn Gly Thr Arg Arg Phe Arg Arg Ser Ile Thr Glu Asn Val Ala
            530                 535                 540

Asn Cys Pro Tyr Val Ser Tyr Gly Lys Phe Cys Ile Lys Pro Asp Gly
545                 550                 555                 560

Ser Ile Ala Thr Ile Val Pro Lys Gln Leu Glu Gln Phe Val Ala Pro
                565                 570                 575

Leu Leu Asn Val Thr Glu Asn Val Leu Ile Pro Asn Ser Phe Asn Leu
            580                 585                 590

Thr Val Thr Asp Glu Tyr Ile Gln Thr Arg Met Asp Lys Val Gln Ile
            595                 600                 605

Asn Cys Met Gln Tyr Val Cys Gly Asn Ser Leu Asp Cys Arg Asp Leu
610                 615                 620

Phe Gln Gln Tyr Gly Pro Val Cys Asp Asn Ile Leu Ser Val Val Asn
625                 630                 635                 640

Ser Ile Gly Gln Lys Glu Asp Met Glu Leu Leu Asn Phe Tyr Ser Ser
                645                 650                 655

Thr Lys Pro Ala Gly Phe Asn Thr Pro Phe Leu Ser Asn Val Ser Thr
            660                 665                 670

Gly Glu Phe Asn Ile Ser Leu Leu Leu Thr Thr Pro Ser Ser Pro Arg
            675                 680                 685

Arg Arg Ser Phe Ile Glu Asp Leu Leu Phe Thr Ser Val Glu Ser Val
690                 695                 700

Gly Leu Pro Thr Asp Asp Ala Tyr Lys Asn Cys Thr Ala Gly Pro Leu
705                 710                 715                 720

Gly Phe Leu Lys Asp Leu Ala Cys Ala Arg Glu Tyr Asn Gly Leu Leu
                725                 730                 735

Val Leu Pro Pro Ile Ile Thr Ala Glu Met Gln Thr Leu Tyr Thr Ser
            740                 745                 750

Ser Leu Val Ala Ser Met Ala Phe Gly Gly Ile Thr Ala Ala Gly Ala
            755                 760                 765

Ile Pro Phe Ala Thr Gln Leu Gln Ala Arg Ile Asn His Leu Gly Ile
            770                 775                 780

Thr Gln Ser Leu Leu Leu Lys Asn Gln Glu Lys Ile Ala Ala Ser Phe
785                 790                 795                 800

Asn Lys Ala Ile Gly Arg Met Gln Glu Gly Phe Arg Ser Thr Ser Leu
                805                 810                 815

Ala Leu Gln Gln Ile Gln Asp Val Val Asn Lys Gln Ser Ala Ile Leu
            820                 825                 830

Thr Glu Thr Met Ala Ser Leu Asn Lys Asn Phe Gly Ala Ile Ser Ser
```

```
                835                 840                 845
Met Ile Gln Glu Ile Tyr Gln Gln Leu Asp Ala Ile Gln Ala Asn Ala
            850                 855                 860
Gln Val Asp Arg Leu Ile Thr Gly Arg Leu Ser Ser Leu Ser Val Leu
865                 870                 875                 880
Ala Ser Ala Lys Gln Ala Glu His Ile Arg Val Ser Gln Gln Arg Glu
                885                 890                 895
Leu Ala Thr Gln Lys Ile Asn Glu Cys Val Lys Ser Gln Ser Ile Arg
            900                 905                 910
Tyr Ser Phe Cys Gly Asn Gly Arg His Val Leu Thr Ile Pro Gln Asn
            915                 920                 925
Ala Pro Asn Gly Ile Val Phe Ile His Phe Ser Tyr Thr Pro Asp Ser
            930                 935                 940
Phe Val Asn Val Thr Ala Ile Val Gly Phe Cys Val Lys Pro Ala Asn
945                 950                 955                 960
Ala Ser Gln Tyr Ala Ile Val Pro Ala Asn Gly Arg Gly Ile Phe Ile
                965                 970                 975
Gln Val Asn Gly Ser Tyr Tyr Ile Thr Ala Arg Asp Met Tyr Met Pro
            980                 985                 990
Arg Ala Ile Thr Ala Gly Asp Ile Val Thr Leu Thr Ser Cys Gln Ala
                995                1000                1005
Asn Tyr Val Ser Val Asn Lys Thr Val Ile Thr Thr Phe Val Asp
            1010                1015                1020
Asn Asp Asp Phe Asp Phe Asn Asp Glu Leu Ser Lys Trp Trp Asn
            1025                1030                1035
Asp Thr Lys His Glu Leu Pro Asp Phe Asp Lys Phe Asn Tyr Thr
            1040                1045                1050
Val Pro Ile Leu Asp Ile Asp Ser Glu Ile Asp Arg Ile Gln Gly
            1055                1060                1065
Val Ile Gln Gly Leu Asn Asp Ser Leu Ile Asp Leu Glu Lys Leu
            1070                1075                1080
Ser Ile Leu Lys Thr Tyr Ile Lys Trp Pro Trp Tyr Val Trp Leu
            1085                1090                1095
Ala Ile Ala Phe Ala Thr Ile Ile Phe Ile Leu Ile Leu Gly Trp
            1100                1105                1110
Val Phe Phe Met Thr Gly Cys Cys Gly Cys Cys Cys Gly Cys Phe
            1115                1120                1125
Gly Ile Met Pro Leu Met Ser Lys Cys Gly Lys Lys Ser Ser Tyr
            1130                1135                1140
Tyr Thr Thr Phe Asp Asn Asp Val Val Thr
            1145                1150

<210> SEQ ID NO 7
<211> LENGTH: 628
<212> TYPE: PRT
<213> ORGANISM: Infectious bronchitis virus

<400> SEQUENCE: 7

Phe Arg Arg Ser Ile Thr Glu Asn Val Ala Asn Cys Pro Tyr Val Ser
1                   5                  10                  15
Tyr Gly Lys Phe Cys Ile Lys Pro Asp Gly Ser Ile Ala Thr Ile Val
                20                  25                  30
Pro Lys Gln Leu Glu Gln Phe Val Ala Pro Leu Phe Asn Val Thr Glu
            35                  40                  45
```

-continued

```
Asn Val Leu Ile Pro Asn Ser Phe Asn Leu Thr Val Thr Asp Glu Tyr
         50                  55                  60
Ile Gln Thr Arg Met Asp Lys Val Gln Ile Asn Cys Leu Gln Tyr Val
 65                  70                  75                  80
Cys Gly Ser Ser Leu Asp Cys Arg Lys Leu Phe Gln Gln Tyr Gly Pro
                 85                  90                  95
Val Cys Asp Asn Ile Leu Ser Val Val Asn Ser Val Gly Gln Lys Glu
                100                 105                 110
Asp Met Glu Leu Leu Asn Phe Tyr Ser Ser Thr Lys Pro Ala Gly Phe
                115                 120                 125
Asn Thr Pro Val Leu Ser Asn Val Ser Thr Gly Glu Phe Asn Ile Ser
            130                 135                 140
Leu Leu Leu Thr Asn Pro Ser Ser Arg Arg Lys Arg Ser Leu Ile Glu
145                 150                 155                 160
Asp Leu Leu Phe Thr Ser Val Glu Ser Val Gly Leu Pro Thr Asn Asp
                165                 170                 175
Ala Tyr Lys Asn Cys Thr Ala Gly Pro Leu Gly Phe Phe Lys Asp Leu
                180                 185                 190
Ala Cys Ala Arg Glu Tyr Asn Gly Leu Leu Val Leu Pro Pro Ile Ile
            195                 200                 205
Thr Ala Glu Met Gln Ala Leu Tyr Thr Ser Ser Leu Val Ala Ser Met
        210                 215                 220
Ala Phe Gly Gly Ile Thr Ala Ala Gly Ala Ile Pro Phe Ala Thr Gln
225                 230                 235                 240
Leu Gln Ala Arg Ile Asn His Leu Gly Ile Thr Gln Ser Leu Leu Leu
                245                 250                 255
Lys Asn Gln Glu Lys Ile Ala Ala Ser Phe Asn Lys Ala Ile Gly His
                260                 265                 270
Met Gln Glu Gly Phe Arg Ser Thr Ser Leu Ala Leu Gln Gln Ile Gln
            275                 280                 285
Asp Val Val Ser Lys Gln Ser Ala Ile Leu Thr Glu Thr Met Ala Ser
        290                 295                 300
Leu Asn Lys Asn Phe Gly Ala Ile Ser Ser Val Ile Gln Glu Ile Tyr
305                 310                 315                 320
Gln Gln Phe Asp Ala Ile Gln Ala Asn Ala Gln Val Asp Arg Leu Ile
                325                 330                 335
Thr Gly Arg Leu Ser Ser Leu Ser Val Leu Ala Ser Ala Lys Gln Ala
            340                 345                 350
Glu Tyr Ile Arg Val Ser Gln Gln Arg Glu Leu Ala Thr Gln Lys Ile
        355                 360                 365
Asn Glu Cys Val Lys Ser Gln Ser Ile Arg Tyr Ser Phe Cys Gly Asn
    370                 375                 380
Gly Arg His Val Leu Thr Ile Pro Gln Asn Ala Pro Asn Gly Ile Val
385                 390                 395                 400
Phe Ile His Phe Ser Tyr Thr Pro Asp Ser Phe Val Asn Val Thr Ala
                405                 410                 415
Ile Val Gly Phe Cys Val Lys Pro Ala Asn Ala Ser Gln Tyr Ala Ile
            420                 425                 430
Val Pro Ala Asn Gly Arg Gly Ile Phe Ile Gln Val Asn Gly Ser Tyr
        435                 440                 445
Tyr Ile Thr Ala Arg Asp Met Tyr Met Pro Arg Ala Ile Thr Ala Gly
    450                 455                 460
Asp Val Val Thr Leu Thr Ser Cys Gln Ala Asn Tyr Val Ser Val Asn
```

```
            465                 470                 475                 480
Lys Thr Val Ile Thr Thr Phe Val Asp Asn Asp Asp Phe Asp Phe Asn
                        485                 490                 495

Asp Glu Leu Ser Lys Trp Trp Asn Asp Thr Lys His Glu Leu Pro Asp
                500                 505                 510

Phe Asp Lys Phe Asn Tyr Thr Val Pro Ile Leu Asp Ile Asp Ser Glu
                515                 520                 525

Ile Asp Arg Ile Gln Gly Val Ile Gln Gly Leu Asn Asp Ser Leu Ile
            530                 535                 540

Asp Leu Glu Lys Leu Ser Ile Leu Lys Thr Tyr Ile Lys Trp Pro Trp
545                 550                 555                 560

Tyr Val Trp Leu Ala Ile Ala Phe Ala Thr Ile Ile Phe Ile Leu Ile
                565                 570                 575

Leu Gly Trp Val Phe Phe Met Thr Gly Cys Cys Gly Cys Cys Cys Gly
                580                 585                 590

Cys Phe Gly Ile Met Pro Leu Met Ser Lys Cys Gly Lys Lys Ser Ser
            595                 600                 605

Tyr Tyr Thr Thr Phe Asp Asn Asp Val Val Thr Glu Gln Tyr Arg Pro
            610                 615                 620

Lys Lys Ser Val
625

<210> SEQ ID NO 8
<211> LENGTH: 619
<212> TYPE: PRT
<213> ORGANISM: Infectious bronchitis virus

<400> SEQUENCE: 8

Phe Arg Arg Ser Ile Thr Glu Asn Val Ala Asn Cys Pro Tyr Val Ser
1               5                   10                  15

Tyr Gly Lys Phe Cys Ile Lys Pro Asp Gly Ser Ile Ala Thr Ile Val
                20                  25                  30

Pro Lys Gln Leu Glu Gln Phe Val Ala Pro Leu Leu Asn Val Thr Glu
            35                  40                  45

Asn Val Leu Ile Pro Asn Ser Phe Asn Leu Thr Val Thr Asp Glu Tyr
    50                  55                  60

Ile Gln Thr Arg Met Asp Lys Val Gln Ile Asn Cys Met Gln Tyr Val
65                  70                  75                  80

Cys Gly Asn Ser Leu Asp Cys Arg Asp Leu Phe Gln Gln Tyr Gly Pro
                85                  90                  95

Val Cys Asp Asn Ile Leu Ser Val Val Asn Ser Ile Gly Gln Lys Glu
            100                 105                 110

Asp Met Glu Leu Leu Asn Phe Tyr Ser Ser Thr Lys Pro Ala Gly Phe
        115                 120                 125

Asn Thr Pro Phe Leu Ser Asn Val Ser Thr Gly Glu Phe Asn Ile Ser
    130                 135                 140

Leu Leu Leu Thr Thr Pro Ser Ser Pro Arg Arg Ser Phe Ile Glu
145                 150                 155                 160

Asp Leu Leu Phe Thr Ser Val Glu Ser Val Gly Leu Pro Thr Asp Asp
                165                 170                 175

Ala Tyr Lys Asn Cys Thr Ala Gly Pro Leu Gly Phe Leu Lys Asp Leu
            180                 185                 190

Ala Cys Ala Arg Glu Tyr Asn Gly Leu Leu Val Leu Pro Pro Ile Ile
        195                 200                 205
```

```
Thr Ala Glu Met Gln Thr Leu Tyr Thr Ser Ser Leu Val Ala Ser Met
            210                 215                 220
Ala Phe Gly Gly Ile Thr Ala Ala Gly Ala Ile Pro Phe Ala Thr Gln
225                 230                 235                 240
Leu Gln Ala Arg Ile Asn His Leu Gly Ile Thr Gln Ser Leu Leu Leu
                245                 250                 255
Lys Asn Gln Glu Lys Ile Ala Ala Ser Phe Asn Lys Ala Ile Gly Arg
            260                 265                 270
Met Gln Glu Gly Phe Arg Ser Thr Ser Leu Ala Leu Gln Gln Ile Gln
            275                 280                 285
Asp Val Val Asn Lys Gln Ser Ala Ile Leu Thr Glu Thr Met Ala Ser
290                 295                 300
Leu Asn Lys Asn Phe Gly Ala Ile Ser Ser Met Ile Gln Glu Ile Tyr
305                 310                 315                 320
Gln Gln Leu Asp Ala Ile Gln Ala Asn Ala Gln Val Asp Arg Leu Ile
                325                 330                 335
Thr Gly Arg Leu Ser Ser Leu Ser Val Leu Ala Ser Ala Lys Gln Ala
                340                 345                 350
Glu His Ile Arg Val Ser Gln Gln Arg Glu Leu Ala Thr Gln Lys Ile
            355                 360                 365
Asn Glu Cys Val Lys Ser Gln Ser Ile Arg Tyr Ser Phe Cys Gly Asn
370                 375                 380
Gly Arg His Val Leu Thr Ile Pro Gln Asn Ala Pro Asn Gly Ile Val
385                 390                 395                 400
Phe Ile His Phe Ser Tyr Thr Pro Asp Ser Phe Val Asn Val Thr Ala
                405                 410                 415
Ile Val Gly Phe Cys Val Lys Pro Ala Asn Ala Ser Gln Tyr Ala Ile
                420                 425                 430
Val Pro Ala Asn Gly Arg Gly Ile Phe Ile Gln Val Asn Gly Ser Tyr
                435                 440                 445
Tyr Ile Thr Ala Arg Asp Met Tyr Met Pro Arg Ala Ile Thr Ala Gly
            450                 455                 460
Asp Ile Val Thr Leu Thr Ser Cys Gln Ala Asn Tyr Val Ser Val Asn
465                 470                 475                 480
Lys Thr Val Ile Thr Thr Phe Val Asp Asn Asp Asp Phe Asp Phe Asn
                485                 490                 495
Asp Glu Leu Ser Lys Trp Trp Asn Asp Thr Lys His Glu Leu Pro Asp
            500                 505                 510
Phe Asp Lys Phe Asn Tyr Thr Val Pro Ile Leu Asp Ile Asp Ser Glu
            515                 520                 525
Ile Asp Arg Ile Gln Gly Val Ile Gln Gly Leu Asn Asp Ser Leu Ile
530                 535                 540
Asp Leu Glu Lys Leu Ser Ile Leu Lys Thr Tyr Ile Lys Trp Pro Trp
545                 550                 555                 560
Tyr Val Trp Leu Ala Ile Ala Phe Ala Thr Ile Ile Phe Ile Leu Ile
                565                 570                 575
Leu Gly Trp Val Phe Phe Met Thr Gly Cys Cys Gly Cys Cys Cys Gly
                580                 585                 590
Cys Phe Gly Ile Met Pro Leu Met Ser Lys Cys Gly Lys Lys Ser Ser
            595                 600                 605
Tyr Tyr Thr Thr Phe Asp Asn Asp Val Val Thr
            610                 615
```

```
<210> SEQ ID NO 9
<211> LENGTH: 6
<212> TYPE: PRT
<213> ORGANISM: Artificial Sequence
<220> FEATURE:
<223> OTHER INFORMATION: Sequence motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: VARIANT
<222> LOCATION: (2)..(3)
<223> OTHER INFORMATION: Xaa is a basic residue
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: VARIANT
<222> LOCATION: (5)..(5)
<223> OTHER INFORMATION: Xaa is a basic residue
<220> FEATURE:
<221> NAME/KEY: misc_feature
<222> LOCATION: (6)..(6)
<223> OTHER INFORMATION: Xaa can be any naturally occurring amino acid

<400> SEQUENCE: 9

Xaa Xaa Xaa Xaa Xaa Xaa
1               5

<210> SEQ ID NO 10
<211> LENGTH: 6
<212> TYPE: PRT
<213> ORGANISM: Artificial Sequence
<220> FEATURE:
<223> OTHER INFORMATION: Portion of the S2 sequence

<400> SEQUENCE: 10

Ser Arg Arg Lys Arg Ser
1               5

<210> SEQ ID NO 11
<211> LENGTH: 6
<212> TYPE: PRT
<213> ORGANISM: Artificial Sequence
<220> FEATURE:
<223> OTHER INFORMATION: Portion of the S2 sequence

<400> SEQUENCE: 11

Ser Arg Arg Arg Arg Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Portion of the S2 sequence

<400> SEQUENCE: 12

Ser Arg Arg Lys Arg Ser Leu Ile Glu
1               5

<210> SEQ ID NO 13
<211> LENGTH: 9
<212> TYPE: PRT
<213> ORGANISM: Artificial Sequence
<220> FEATURE:
<223> OTHER INFORMATION: Portion of the S2 sequence
```

```
<400> SEQUENCE: 13

Ser Arg Arg Arg Arg Ser Val Ile Glu
1               5
```